(12) United States Patent
Chen et al.

(10) Patent No.: US 10,150,095 B2
(45) Date of Patent: Dec. 11, 2018

(54) POROUS METAL-ORGANIC FRAMEWORK WITH PYRIMIDINE GROUPS FOR METHANE STORAGE EXHIBITING HIGH WORKING CAPACITY

(71) Applicant: The Board of Regents of the University of Texas System, Austin, TX (US)

(72) Inventors: Banglin Chen, San Antonio, TX (US); Bin Li, San Antonio, TX (US); Hui-Min Wen, San Antonio, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 125 days.

(21) Appl. No.: 15/127,514

(22) PCT Filed: Mar. 20, 2015

(86) PCT No.: PCT/US2015/021691
§ 371 (c)(1),
(2) Date: Sep. 20, 2016

(87) PCT Pub. No.: WO2015/143286
PCT Pub. Date: Sep. 24, 2015

(65) Prior Publication Data
US 2017/0173559 A1 Jun. 22, 2017

Related U.S. Application Data

(60) Provisional application No. 61/968,849, filed on Mar. 21, 2014.

(51) Int. Cl.
| | |
|---|---|
| B01J 20/22 | (2006.01) |
| B01D 53/02 | (2006.01) |
| C07D 239/26 | (2006.01) |
| C07C 7/12 | (2006.01) |
| B01J 31/16 | (2006.01) |
| C07F 1/08 | (2006.01) |
| B01J 20/28 | (2006.01) |
| B01J 31/18 | (2006.01) |

(52) U.S. Cl.
CPC ............ *B01J 20/226* (2013.01); *B01D 53/02* (2013.01); *B01J 20/28066* (2013.01); *B01J 20/28076* (2013.01); *B01J 31/1691* (2013.01); *B01J 31/1815* (2013.01); *C07C 7/12* (2013.01); *C07D 239/26* (2013.01); *C07F 1/08* (2013.01); *B01D 2253/202* (2013.01); *B01D 2253/204* (2013.01); *B01D 2256/14* (2013.01); *B01D 2256/16* (2013.01); *B01D 2257/504* (2013.01); *B01D 2257/7022* (2013.01); *B01J 2531/0216* (2013.01); *B01J 2531/0219* (2013.01); *B01J 2531/16* (2013.01); *Y02C 10/08* (2013.01); *Y02P 20/152* (2015.11)

(58) Field of Classification Search
CPC .. B01J 20/226; B01D 53/02; B01D 2253/202; B01D 2257/7022; B01D 2257/504; B01D 2256/14; C07C 7/12; C07D 239/26
See application file for complete search history.

(56) References Cited

U.S. PATENT DOCUMENTS

| | | |
|---|---|---|
| 5,648,508 A | 7/1997 | Yaghi |
| 9,120,080 B2 | 9/2015 | Chen |
| 2006/0252641 A1 | 11/2006 | Yaghi et al. |

(Continued)

OTHER PUBLICATIONS

Li Bin et al., A Porous Metal Organic Framework With Dynamic Pyrimidine Groups Exhibiting Record High Methane Storage Working Capacity, Journal of the American Chemical Society, 136(17), 6207-6210, (2014).*

Chen et al., "A New Multidentate Hexacarboxylic Acid for the Construction of Porous Metal—Organic Frameworks of Diverse Structures and Porosities," *Cryst. Growth Des.*, 10, 2775-2779, 2010.

Chen et al., "High $H_2$ Adsorption in a Microporous Metal—Organic Framework with Open Metal Sites," *Angew. Chem., Int. Ed.*, 44, 4745, 2005.

Chui et al., "A Chemically Functionalizable Nanoporous Material $[Cu_3(TMA)_2(H_2O)_3]$," *Science*, 283, 1148, 1999.

(Continued)

*Primary Examiner* — Alexander R Pagano
*Assistant Examiner* — Ebenezer O Sackey
(74) *Attorney, Agent, or Firm* — Parker Highlander PLLC

(57) ABSTRACT

Disclosed herein are metal-organic frameworks (MOF) and uses thereof, including those comprising a repeat unit of the formula $[Cu_2L(H_2O)_2]$-5DMF-3$H_2O$, wherein L is a ligand of the formula: These are useful for many applications, including in the purification of hydrogen gas from production byproducts $CH_4$ and $CO_2$, sensing, heterogeneous catalysis, drug delivery, lithium sulfide battery, membrane and analytical devices.

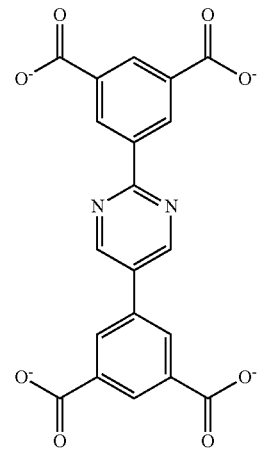

20 Claims, 16 Drawing Sheets

(56) References Cited

U.S. PATENT DOCUMENTS

2007/0248852 A1   10/2007   Mueller et al.
2012/0172612 A1*   7/2012   Yaghi ................... C07C 63/331
                                                                                                556/132
2013/0035527 A1    2/2013   Chen

OTHER PUBLICATIONS

Eddaoudi et al., "Systematic Design of Pore Size and Functionality in Isoreticular MOFs and Their Application in Methane Storage," *Science*, 295, 469, 2002.

Feldblyum et al., "Interpenetration, Porosity, and High-Pressure Gas Adsorption in $Zn_4O(2,6$-naphthalene dicarboxylate$)_3$," *Langmuir*, 29, 8146, 2013.

Férey et al., "Large breathing effects in three-dimensional porous hybrid matter: facts, analyses, rules and consequences," *Chem. Soc. Rev.*, 38, 1380, 2009.

Furukawa et al., "The Chemistry and Application of Metal-Organic Frameworks," *Science*, 341:974, 2013.

Gedrich et al., "A Highly Porous Metal-Organic Framework with Open Nickel Sites," *Angew. Chem., Int. Ed.*, 49, 8489, 2010.

Guo et al., "A Metal-Organic Framework with Optimized Open Metal Sites and Pore Spaces for High Methane Storage at Room Temperature," *Angew. Chem., Int. Ed*, 50, 3178.

He et al., "A series of metal-organic frameworks with high methane uptake and an empirical equation for predicting methane storage capacity," *Energy Environ. Sci.*, 6, 2735, 2013.

He et al., "Microporous metal-organic frameworks for storage and separation of small hydrocarbons," *Chem. Commun.*, 48, 11813, 2012.

Horike et al., "Soft porous crystals," *Nat. Chem.*, 1, 695, 2009.

International Preliminary Report on Patentability issued in corresponding PCT Application No. PCT/US2015/021691, dated Jun. 17, 2015.

International Preliminary Report on Patentability issued in corresponding PCT Application No. PCT/US2010/023773, dated Aug. 23, 2012.

International Search Report and Written Opinion issued in corresponding PCT Application No. PCT/US2015/021691, dated Jun. 17, 2015.

Jiang and Xu, "Porous metal-organic frameworks as platforms for functional applications," *Chem. Commun.*, 47, 3351-3370, 2011.

Kondo et al., "Three-Dimensional Framework with Channeling Cavities for Small Molecules: $\{[M_2(4, 4'\text{-bpy})_3(NO_3)_4] \cdot xH_2O\}_n$ (M=Co, Ni, Zn)," *Angew. Chem., Int. Ed.*, 36, 1725, 1997.

Kong et al., "Expanded Organic Building Units for the Construction of Highly Porous Metal-Organic Frameworks," *Chem. Eur. J.*, 19, 14886, 2013.

Lin et al., "High $H_2$ Adsorption by Coordination-Framework Materials," *Angew. Chem., Int. Ed.*, 45, 7358, 2006.

Ma et al., "Metal-Organic Framework from an Anthracene Derivative Containing Nanoscopic Cages Exhibiting High Methane Uptake," *J. Am. Chem. Soc.*, 130, 1012, 2008.

Makal et al., "Methane storage in advanced porous materials," *Chem. Soc. Rev.*, 41, 7761, 2012.

Mason et al., "Evaluating metal-organic frameworks for natural gas storage," *Chem. Sci.*, 5, 32, 2014.

Matsuda et al., "Highly controlled acetylene accommodation in a metal-organic microporous material," *Nat. Lett.* 436(14):238-241, 2005.

O'Keeffe et al., "Deconstructing the Crystal Structures of Metal-Organic Frameworks and Related Materials into Their Underlying Nets," *Chem. Rev.*, 112, 675 2012.

Park and Suh, "Enhanced isosteric heat, selectivity, and uptake capacity of $CO_2$ adsorption in a metal-organic framework by impregnated metal ions," *Chem. Sci.*, 4, 685, 2013.

Park et al., "Introduction of Functionalized Mesopores to Metal-Organic Frameworks via Metal-Ligand-Fragment Coassembly," *J. Am. Chem. Soc.*, 134, 20110, 2012.

Peng et al., "Methane Storage in Metal-Organic Frameworks: Current Records, Surprise Findings, and Challenges," *J. Am. Chem. Soc.*, 135, 11887, 2013.

Sumida et al., "Carbon Dioxide Capture in Metal-Organic Frameworks," *Chem. Rev.*, 112, 724, 2012.

Wang et al., "Metal-Organic Frameworks as a Tunable Platform for Designing Functional Molecular Materials," *J. Am. Chem. Soc.*, 135, 13222, 2013.

Wilmer et al., "Gram-scale, high-yield synthesis of a robust metal-organic framework for storing methane and other gases," *Energy Environ. Sci.*, 6, 1158, 2013.

Wilmer et al., "Large-scale screening of hypothetical metal-organic frameworks," *Nat. Chem.* 4:83-89, 2011.

Wu et al., "Commensurate Adsorption of Hydrocarbons and Alcohols in Microporous Metal Organic Frameworks," *Chem. Rev.*, 112, 836, 2012.

Wu et al., "High-Capacity Methane Storage in Metal—Organic Frameworks $M_2$(dhtp): The Important Role of Open Metal Sites," *J. Am. Chem. Soc.*, 131, 4995, 2009.

Wu et al., "Unusual and Highly Tunable Missing-Linker Defects in Zirconium Metal-Organic Framework UiO-66 and Their Important Effects on Gas Adsorption," *J. Am. Chem. Soc.*, 135, 10525, 2013.

Wu et al., W. "Metal-organic frameworks with exceptionally high methane uptake: where and how is methane stored?"*Chem.-Eur. J.*, 16, 5205, 2010.

Xiang et al., "Exceptionally high acetylene uptake in a microporous metal-organic framework with open metal sites," *J. Am. Chem. Soc.*, 131(34):12415-12419, 2009.

Xiao et al., "High-capacity hydrogen and nitric oxide adsorption and storage in metal-organic framework," *J. Am. Chem. Soc.* 129:1203-1209, 2007.

Yan et al., "Studies on Metal-Organic Frameworks of Cu(II) with Isophthalate Linkers for Hydrogen Storage,"*Acc. Chem. Res.*, 47(2):296-307, 2014.

Zhang et al., "Metal Azolate Frameworks: From Crystal Engineering to Functional Materials," *Chem. Rev.*, 112, 1001, 2012.

\* cited by examiner

POROUS METAL-ORGANIC FRAMEWORK WITH PYRIMIDINE GROUPS FOR METHANE STORAGE EXHIBITING HIGH WORKING CAPACITY

This application is a national phase application under 35 U.S.C. § 371 of International Application No. PCT/US2015/021691, filed Mar. 20, 2015, which claims the benefit of U.S. Provisional Patent Application No. 61/968,849, filed on Mar. 21, 2014. The entire text of the above referenced disclosures is specifically incorporated herein by reference.

BACKGROUND OF THE INVENTION

I. Field of the Invention

The present disclosure relates generally to the fields of chemistry and materials science. More particularly, it concerns metal-organic frameworks, compositions thereof and methods use thereof, including for separating gas molecules, sensing, heterogeneous catalysis, drug delivery, lithium sulfide battery, membrane and analytical devices.

II. Description of Related Art

Microporous metal-organic frameworks (MOFs) have emerged as a new type of porous materials for gas storage, separation, sensing and heterogeneous catalysis. The tunable pores and the immobilized functional sites within such microporous MOFs have enabled them to direct specific recognition of certain molecules based upon size and functionality.

Control of pore sizes and pore surfaces within porous materials is useful for their ability to selective recognize and thus separation of small molecules, and the pores within such porous MOFs can be systematically modified simply by the change the secondary building blocks (SBUs), changing the organic bridging linkers, or the control of the framework interpenetration (Deng et al., 2010; Chen et al., 2010; Ma et al., 2010; Horike et al., 2009). To tune the micropores to induce their size specific encapsulation of small gas molecules, various series of microporous metal-organic framework materials have emerged as promising microporous media for the recognition and separation of small gas molecules (Kitaura et al., 2004; Chen et al., 2004; Cho et al., 2006; Liu et al., 2010; Murray et al., 2010; Ma et al., 2009; McKinlay et al., 2008; Dubbeldam et al., 2008; Chen et al., 2006; Finsy et al., 2008; Bae et al., 2010; Zhang et al., 2008; Dybtsev et al., 2004; Li et al., 2009; Vaidhyanathan et al., 2006; Nuzhdin et al., 2007; Dybtsev et al., 2006; Chen et al., 2008).

The discovery of new energy resources, particularly natural gas in the form of shale gas in the United States, is facilitating the implementation of natural gas as a viable alternative energy source. The United States has the commercialization capability to produce large-scale shale gas at a cheaper cost than other countries, which makes natural gas appealing as a new fuel (Armor, 2013). In order to accelerate such a fuel switching from coal/petroleum to natural gas, suitable materials for natural gas storage and transportation need to be developed. While Compressed Natural Gas (CNG), stored as supercritical fluid at room temperature and 200-300 bar in steel cylinder, might be still suitable for large vehicles such as trucks, Adsorbed Natural Gas (ANG) is better suited for daily use cars for both the cost and safety reasons.

Among the diverse porous adsorbents for methane storage (methane is the main component in natural gas), porous metal-organic frameworks (MOFs) are promising for such a purpose because of their high porosities, tunable pores and easily immobilized functional sites to optimize their storage capacities (O'Keeffe et al., 2012; Horike et al., 2009; Férey and Serre, 2009; Zhang et al., 2012; Yan et al., 2013; Wang et al., 2013; Sumida et al., 2012; Getman et al., 2012; Wu et al., 2012; Wilmer et al., 2013; Wu et al., 2009; Park and Suh, 2013 and Jiang and Xu, 2011). BASF has commercialized some prototypic MOFs as well as demonstrated model vehicles fueled with natural gas by making use of BASF MOF materials (BASF MOF Materials for Energy Storage). In order to fully implement natural gas fuel systems for vehicles, target adsorbents with high methane storage capacities need to be developed. The Advanced Research Projects Agency-Energy (ARPA-E) of the U.S. Department of Energy (DOE) developed methane storage targets to guide the research on adsorbent based methane storage with the goal of a volumetric storage capacity of 350 $cm^3$ (STP) $cm^{-3}$ for the adsorbent material at room temperature (DOE MOVE Guidelines). Without the consideration of packing loss, according to the guidelines, the volumetric storage capacity needs to be higher than 263 $cm^3$ (STP) $cm^{-3}$, equivalent to that of CNG at 250 bar and 298 K. Furthermore, the DOE set a target of the gravimetric energy density of 0.5 g ($CH_4$) $g^{-1}$ (adsorbent) for new adsorbent based methane storage materials.

Although the potential of MOF materials for methane storage has been conceptually established, reaching the DOE targets in practice has been challenging. Since the discovery of the first MOFs for methane storage, (Kondo et al., 1997 and Eddaoudi et al., 2002) significant progress has been made to improve the methane storage capacities of MOF materials over the past decade; however, their storage capacities are still far away from the DOE target (He et al., 2012 and Makal et al., 2012). Recently, three independent groups realized a unique MOF, HKUST-1 (Chui et al., 1999), for high methane storage with volumetric storage capacity of 259-267 $cm^3$ (STP) $cm^{-3}$ at 65 bar and room temperature (Peng et al., 2013 and Mason et al., 2014). This was the first MOF material whose volumetric methane storage capacity to reach the DOE target if packing loss is not considered.

The saturated gravimetric methane storage capacities of MOF materials are basically determined by their porosities (pore volumes and/or BET surface areas) (Peng et al., 2013; He et al., 2013; Kong et al., 2013 and Feldblyum et al., 2013). In order to optimize volumetric methane storage capacities, MOFs balance porosities and framework densities with a high densities of functional sites/groups and pore cages for the recognition of methane molecules (He et al., 2013; Gedrich et al., 2010; Ma et al., 2008 and Guo et al., 2011). The MOF-505 series of MOFs of NbO type structures meet these criteria and are of interest (Chen et al., 2005 and Lin et al., 2006).

SUMMARY OF THE INVENTION

In some aspects, the invention provides a metal-organic framework (MOF) comprising a repeat unit of the formula $[Cu_2L(H_2O)_2]\cdot5DMF\cdot3H_2O$ (UTSA-76), wherein L is a ligand of the formula or a protonated, unprotonated, partially protonated, or partially unprotonated form thereof:

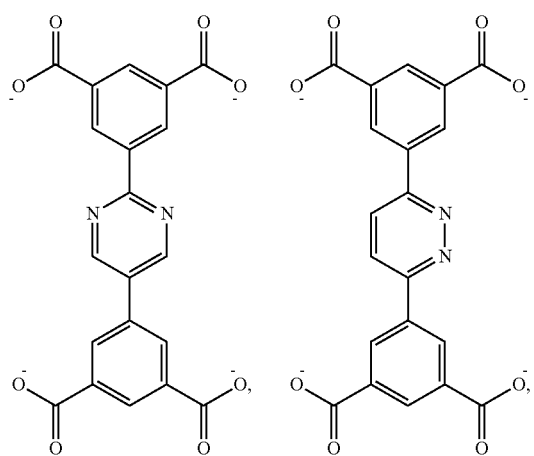
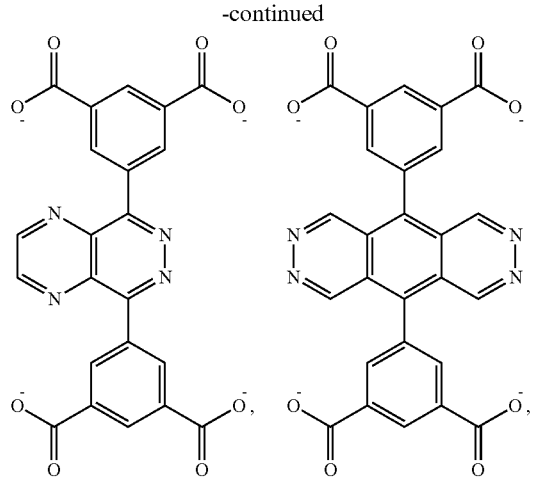
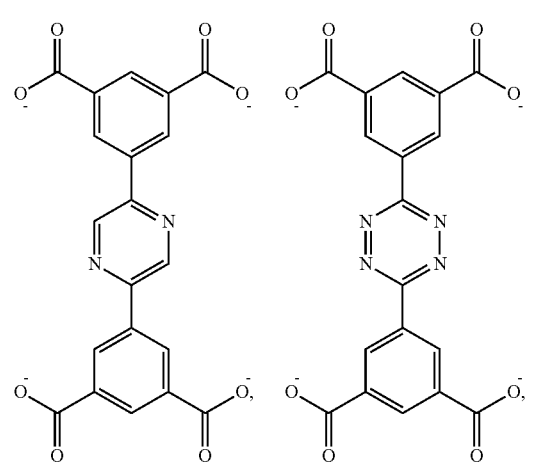
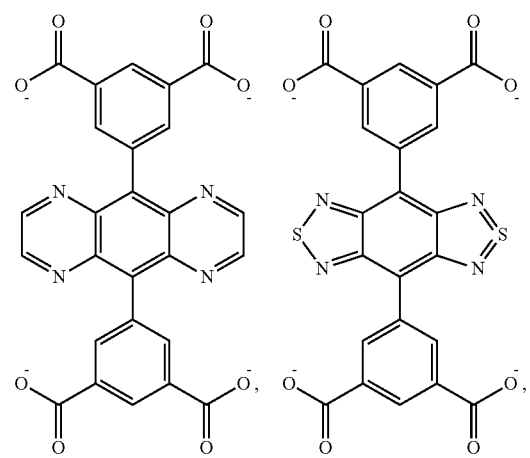
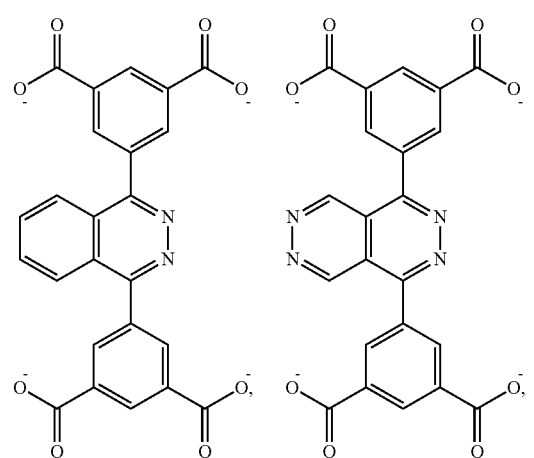
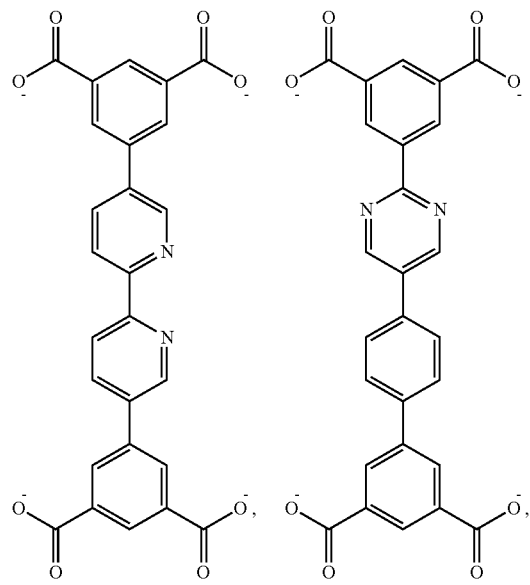

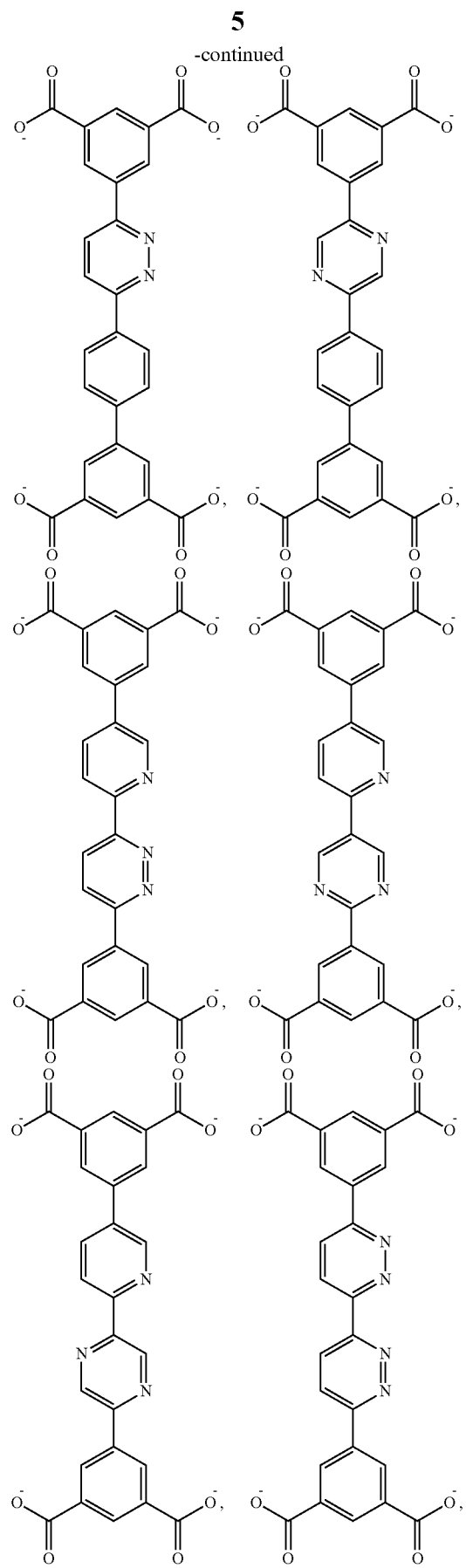
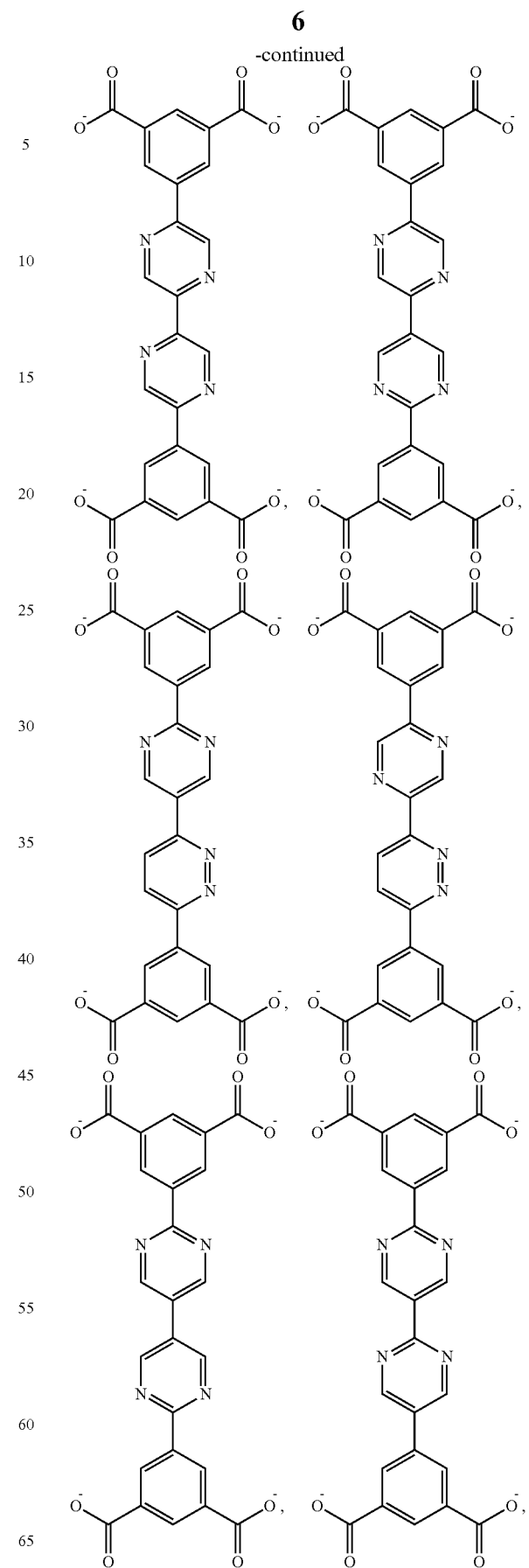

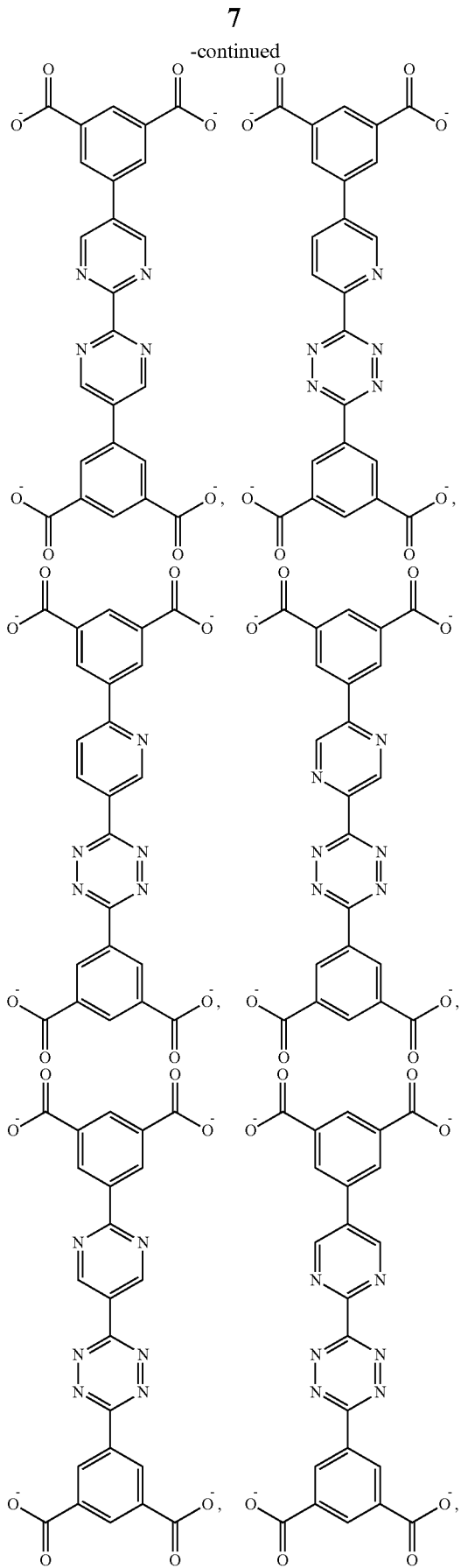
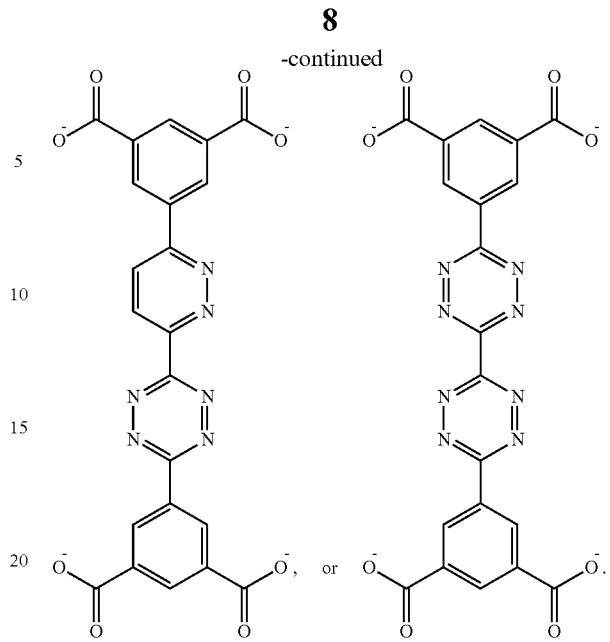

In some embodiments, the metal organic framework is activated for sorption of gas molecules. In some embodiments, the MOF further comprises one or more than one type of guest molecule. In some embodiments, the guest molecule is a solvent molecule. In some embodiments, the solvent molecule is water. In other embodiments, the solvent molecule is N,N'-dimethylformamide.

In some embodiments, the MOF further comprises about between one and eight N,N'-dimethylformamide and between one and eight water molecules per repeat unit. In other embodiments, the MOF is further comprised of about five N,N'-dimethylformamide and three water molecules per repeat unit. In some cases, the solvent molecules occupy the pores of the MOF. In some embodiments, the MOF has the formula: $[Cu_2L(H_2O)_2] \cdot 5DMF \cdot 3H_2O$.

In some embodiments, one type of guest molecule is a gas molecule. In some cases, the gas molecule is $H_2$, $CO_2$, or $CH_4$. In some embodiments, the gas molecule is $CO_2$. In some embodiments, the gas molecule is $CH_4$. In other embodiments, the gas molecule is $H_2$. In other cases, the gas molecule is $CO_2$ and $CH_4$.

In some instances, MOF is substantially free of solvent molecules.

In some cases, the MOF has a weight percentage at least 90% attributable to repeat units of the formula $[Cu_2L(H_2O)_2] \cdot 5DMF \cdot 3H_2O$. In other cases, the MOF has a weight percentage at least 95% attributable to repeat units of the formula $[Cu_2L(H_2O)_2] \cdot 5DMF \cdot 3H_2O$. In some cases, the MOF has a weight percentage at least 99% attributable to repeat units of the formula $[Cu_2L(H_2O)_2] \cdot 5DMF \cdot 3H_2O$. In other instances, the metal-organic framework has been adhered to a fixed surface.

In some embodiments, the repeat unit of the MOF is a ligand of the formula listed in Additional Ligands.

In another aspect, the invention provides methods of separating two or more compounds using an MOF comprising:

(a) obtaining a metal-organic framework (MOF) comprising a repeat unit of the formula $[Cu_2L(H_2O)_2] \cdot 5DMF \cdot 3H_2O$, wherein L is a ligand of formula:

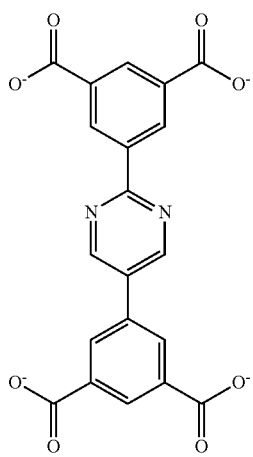

(b) combining the MOF with a mixture comprising a first compound and a second compound; and (c) separating the first compound from the second compound.

In some embodiments, the MOF is activated for sorption of gas molecules. In some embodiments, the separation is based on their differential sorption rate within the MOF.

In some embodiments, the first compound is a gas molecule. In some embodiments, the first compound is $H_2$. In some embodiments, the second compound is a gas molecule. In some embodiments, the second compound is $CH_4$ or $CO_2$. In some embodiments, the second compound is $CH_4$. In other embodiments, the second compound is $CO_2$. In some embodiments, the mixture further comprises a third compound. In some embodiments, the third compound is $CH_4$. In other embodiments, the third compound is $CO_2$. In some embodiments, the mixture comprises $H_2$ and $CH_4$. In other embodiments, the mixture comprises $H_2$ and $CO_2$. In other embodiments, the mixture comprises $H_2$, $CH_4$, and $CO_2$.

In some embodiments, the separation is carried out at a pressure from about 10 kPa to about 50 mPa. In some cases, the separation is carried out at a pressure from about 2 mPa to about 20 mPa. In some embodiments, the separation is carried out at a pressure from about 4 mPa to about 15 mPa In some embodiments, the MOF is adhered to a fixed bed surface. In some embodiments, the MOF is packed in an absorber. In some embodiments, the absorption is carried out at a temperature from about −50° C. to about 50° C.

In other aspect, the invention provides methods of using the MOFs provided herein for sensing, heterogeneous catalysis, drug delivery, and as a component of, for example, a lithium sulfide battery, a membrane, and/or an analytical device.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

FIG. 5 shows a comparison of the total methane uptake at different temperature of UTSA-76a and NOTT-101a.

FIG. 6 shows the comparison of the total volumetric (top) and gravimetric (bottom) methane uptake at 298 K of UTSA-76a and NOTT-101a.

DESCRIPTION OF ILLUSTRATIVE EMBODIMENTS

I. Definitions

Figure 1:
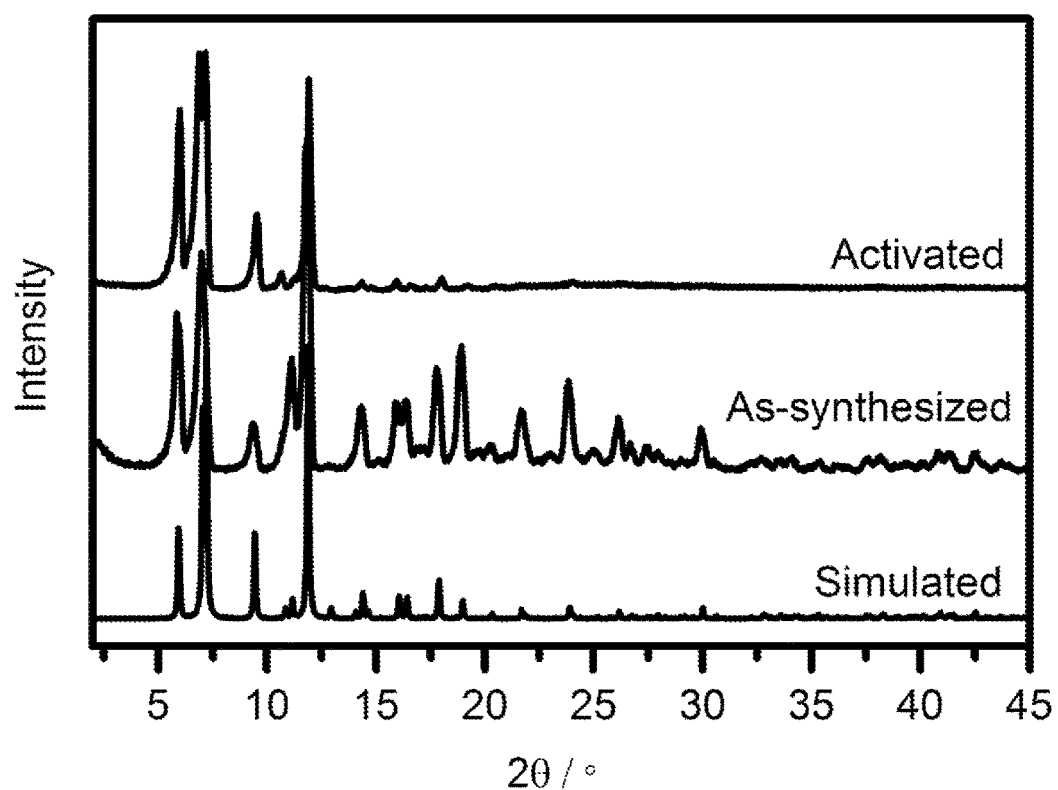
FIG. 1 shows PXRD patterns of as-synthesized UTSA-76 (middle) and activated UTSA-76a (top) along with the simulated XRD pattern from the single-crystal X-ray structure (bottom).

"Metal-organic frameworks" (MOFs) are framework materials, typically three-dimensional, self-assembled by the coordination of metal ions with organic linkers exhibiting porosity, typically established by gas adsorption. The MOFs discussed and disclosed herein are at times simply identified by their repeat unit as defined below without brackets or the subscript n. A mixed-metal-organic frameworks (M'MOF) is a subset of MOFs having two of more types of metal ions.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, —[—$CH_2CH_2$—]$_n$—, the repeat unit is —$CH_2CH_2$—. The subscript "n" denotes the degree of polymerisation, that is, the number of repeat units linked together. When the value for "n" is left undefined, it simply designates repetition of the formula within the brackets as well as the polymeric and/or framework nature of the material. The concept of a repeat unit applies equally to where the connectivity between the repeat units extends into three dimensions, such as in metal organic frameworks, cross-linked polymers, thermosetting polymers, etc. Note that for MOFs the repeat unit may also be shown without the subscript n.

"Pores" or "micropores" in the context of metal-organic frameworks are defined as open space within the MOFs; pores become available, when the MOF is activated for the storage of gas molecules. Activation can be achieved by heating, e.g., to remove solvent molecules.

"Multimodal size distribution" is defined as pore size distribution in three dimensions.

"Multidentate organic linker" is defined as ligand having several binding sites for the coordination to one or more metal ions.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Any undefined valency on a carbon atom of a structure shown in this application implicitly represents a hydrogen atom bonded to the atom.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

The term "saturated" when referring to an atom means that the atom is connected to other atoms only by means of single bonds.

The above definitions supersede any conflicting definition in any of the reference that is incorporated herein by reference. The fact that certain terms are defined, however, should not be considered as indicative that any term that is undefined is indefinite. Rather, all terms used are believed to describe the invention in terms such that one of ordinary skill can appreciate the scope and practice the present invention.

Example 1: Methods and Materials

1. General Procedures and Materials.

All reagents and solvents were commercially available and used without further purification. Dimethyl 5-(4,4,5,5-tetramethyl-1,3,2-dioxaborolan-2-yl) isophthalate was prepared according to the literature procedure (Chen et al., 2010). $^1H$ NMR spectra were recorded on a Varian Mercury 500 MHz spectrometer using tetramethylsilane (TMS) as internal standards. The coupling constants reported in Hertz. FTIR spectra were performed on a Bruker Vector 22 spectrometer at room temperature. The elemental analyses were performed with Perking Elmer 240 CHN analyzers from Galbraith Laboratories, Knoxville. Thermogravimetric analyses (TGA) were carried out using a Shimadzu TGA-50 analyzer under a nitrogen atmosphere with a heating rate of 5° C. $min^{-1}$. Powder X-ray diffraction (PXRD) patterns were measured by a Rigaku Ultima IV diffractometer operated at 40 kV and 44 mA with a scan rate of 1.0 deg $min^{-1}$. The neutron scattering experiment was performed on the High Flux Backscattering Spectrometer at the NIST Center for Neutron Research, which has an incident neutron wavelength of 6.27 Å (2.08 meV) and a resolution of 0.8 meV eV full width at half maximum (FWHM) (Meyer et al., 2003). Elastic neutron scattering intensities were scanned in the T range of 10 K-320 K, with a ramping rate of 1 K/min.

2. Gas Sorption Measurements.

A Micromeritics ASAP 2020 surface area analyzer was used to measure gas adsorption isotherms. To remove all the guest solvents in the framework, the fresh sample of UTSA-76 was guest-exchanged with dry acetone at least 10 times, filtered and degassed at room temperature (296 K) for one day, and then at 373 K for another 20 hours until the outgas rate was 5 μmHg min-1 prior to measurements. The activated sample of UTSA-76a was maintained at 77 K with liquid nitrogen. High-pressure CH4 sorption isotherms were measured using a Sieverts-type apparatus. A detailed description of the experimental setup, calibration, and the isotherm can be found in a previous publication (Meyer et al., 2003).

3. Single-Crystal X-Ray Crystallography.

The crystal data were collected on an Agilent Supernova CCD diffractometer equipped with a graphite-monochromatic enhanced Cu Kα radiation (λ=1.54184 Å) at 100 K. The datasets were corrected by empirical absorption correction using spherical harmonics, implemented in the SCALE3 ABSPACK scaling algorithm. The structure was solved by direct methods and refined by full matrix least-squares methods with the SHELX-97 program package (Zhou et al., 2007). The central pyrimidine ring of organic ligand is disordered, which was refined as disordered model with occupancies of 0.25 for C7, 0.25 for N1, 0.25 for C7', and 0.25 for N1'. The solvent molecules in the compound are highly disordered. The SQUEEZE subroutine of the PLATON software suit was used to remove the scattering from the highly disordered guest molecules (Sheldrick, 1997). The resulting new files were used to further refine the structures. The H atoms on C atoms were generated geometrically.

Example 2: Synthetic Methods

Figure 2:
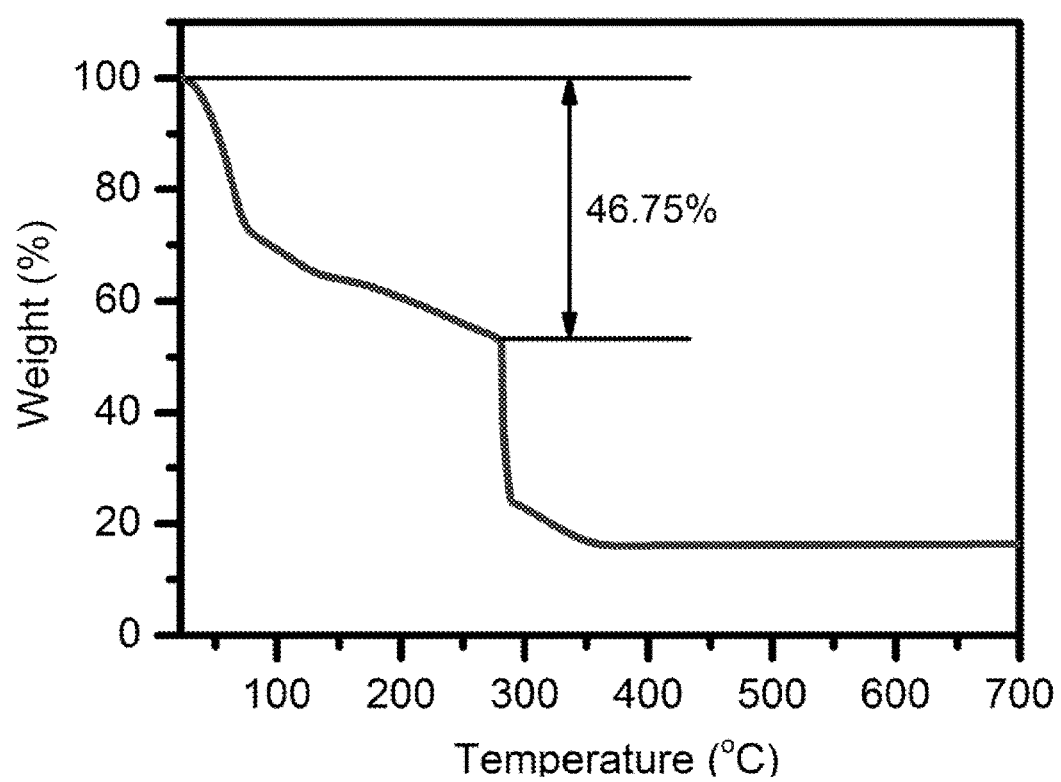
FIG. 2 shows TGA curves of as-synthesized UTSA-76.

Disclosed herein are the synthesis, structures, and sorption studies of one new MOFs, $[Cu_2L(H_2O)_2]\cdot 5DMF\cdot 3H_2O$ (UTSA-76). The organic linker $H_4L$ was readily synthesized by Suzuki cross-coupling reaction of 2,5-dibromopyrimidine and 5-(4,4,5,5-tetramethyl-1,3,2-dioxaborolan-2-yl) isophthalate followed by hydrolysis and acidification in good yield. UTSA-76 was synthesized by a solvothermal reaction of $H_4L$ and $Cu(NO_3)_2\cdot 2.5H_2O$ in DMF/$H_2O$/MeCN mixture solvents with the addition of a small amount of hydrochloric acid at 80° C. for 1 days to afford blue block crystals. The formula was determined as $[Cu_2L(H_2O)_2]\cdot 5DMF\cdot 3H_2O$ by single-crystal X-ray diffraction analysis, thermogravimetric analysis (TGA, FIG. 1) and the elemental analysis. The phase purity of the bulk material was confirmed by powder X-ray diffraction (PXRD, FIG. 2).

Scheme 2. Synthetic routes to the organic linker $H_4L$.

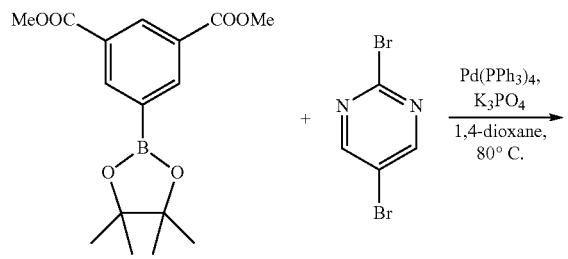

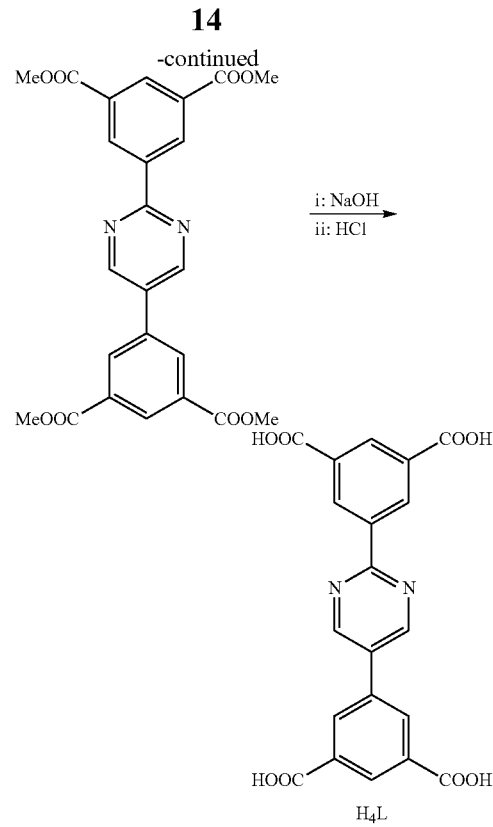

Tetramethyl 5,5'-(pyrimidine-2,5-diyl)diisophthalate 2,5-Dibromopyrimidine (1.18 g, 5 mmol), 5-(4,4,5,5-tetramethyl-1,3,2-dioxaborolan-2-yl) isophthalate (3.52 g, 11 mmol), $K_3PO_4$ (2.55 g, 12 mmol) and tetrakis(triphenylphosphine) palladium(0) (0.3 g, 0.26 mmol) were dissolved in dry 1,4-dioxane (80 mL) under $N_2$ atmosphere. The mixture was stirred at 80° C. for two days. After that, the precipitate was collected by filtration, washed with 1,4-dioxane for several times, and then recrystallized in toluene to obtain the pure product. Yield: 56% (1.3 g). $^1H$ NMR (500 MHz, $CDCl_3$, ppm): δ 9.38 (s, 2H), 9.15 (s, 2H), 8.86 (s, 1H), 8.80 (s, 1H), 8.53 (s, 2H), 4.03 (s, 12H).

5,5'-(pyrimidine-2,5-diyl)diisophthalic acid ($H_4L$)

Tetramethyl 5,5'-(pyrimidine-2,5-diyl)diisophthalate (1.3 g, 2.8 mmol) was suspended in 50 mL THF, and then a 2M KOH aqueous solution (75 mL) was added. The mixture was stirred under reflux overnight until it became clear. After that THF was removed under reduced pressure and dilute HCl was then added to the remaining aqueous solution to acidify pH=2. The precipitate was collected by filtration, washed with water for several times, and dried to afford white powder. Yield: 1.08 g (95%). $^1H$ NMR (500 MHz, DMSO-$d_6$, ppm): δ=13.11 (s, 4H), 9.31 (s, 2H), 9.13 (s, 2H), 8.54 (s, 1H), 8.50 (s, 2H), 8.50 (s, 1H). $^{13}C$ NMR (DMSO-$d_6$, ppm): δ=166.69, 166.65, 161.42, 156.24, 137.96, 135.20, 132.79, 132.57, 132.36, 131.95, 130.80, 130.45.

Synthesis of UTSA-76.

A mixture of the organic linker $H_4L$ (15.0 mg, 0.037 mmol) and $Cu(NO_3)_2\cdot 2.5H_2O$ (30.0 mg, 0.129 mmol) was dissolved into a 8 mL mixed solvent (DMF/MeCN/$H_2O$, 6/1/1, v/v) in a screw-capped vial (20 mL). 50 μL of 37%

HCl were added. The vial was capped and heated in an oven at 80° C. for 24 h. Blue block crystals were obtained by filtration and washed with DMF several times to afford UTSA-76 in 65% yield. UTSA-76 has a formula of [Cu$_2$L(H$_2$O)$_2$].5DMF.3H$_2$O, which was obtained based on the basis of single-crystal X-ray structure determination, elemental analysis and TGA. Anal. Calcd for C$_{35}$H$_{53}$N$_7$O$_{18}$Cu$_2$: C, 42.59; H, 5.41; N, 9.93. found: C, 42.28; H, 5.34; N, 9.98. TGA data for loss of 5DMF and 5H$_2$O: calcd: 46.22%. found: 46.75%. IR (neat, cm$^{-1}$): 1652, 1625, 1591, 1442, 1381, 1362, 1247, 1091, 770, 755, 728, 659.

Single-crystal X-ray diffraction analysis revealed that UTSA-76 crystallizes in the R-3m space group. The framework was consistent with a paddlewheel dinuclear Cu$_2$(COO)$_4$ secondary building units (SBUs) which are bridged by the carboxylates of L$^{4-}$ to form a 3D NbO-type structure. There were two types of cages in the resulting framework. One small cage of about 10.5 Å in diameter is composed of 12 ligands connecting 6 paddlewheel SBUs. One of two nitrogen atoms in each ligand was directed towards this cage, which makes it contain a high density of Lewis basic sites. Another large irregular elongated cage consisted of 6 ligands connecting 12 paddlewheel SBUs. Similarly, this cage also has a high density of Lewis basic sites. Without wishing to be bound by any theory, these two cages with suitable pore sizes and high density of Lewis basic sites may play an important role for the methane storage. Table 1 shows crystallographic data shows structure refinement results for UTSA-76.

TABLE 1

Crystallographic data and structure refinement results for UTSA-76.

| | UTSA-76 |
|---|---|
| Formula | C$_{20}$H$_8$CU$_2$N$_2$O$_{11}$ |
| Formula weight | 579.36 |
| Temperature/K | 100.00(19) |
| Crystal system | Trigonal |
| Space group | R-3m |
| a, b (Å) | 18.6895(5) |
| c (Å) | 37.6886(9) |
| α (°) | 90.00 |
| β (°) | 90.00 |
| γ (°) | 120.00 |
| V (Å$^3$) | 11400.8(5) |
| Z | 9 |
| D$_{calcd}$ (g cm$^{-3}$) | 0.759 |
| μ (mm$^{-1}$) | 0.868 |
| F(000) | 2592.0 |
| Crystal size/mm$^3$ | 0.42 × 0.35 × 0.20 |
| GOF | 1.108 |
| R$_{int}$ | 0.0338 |
| R$_1$, wR$_2$ [I >= 2σ (I)] | 0.0808, 0.2558 |
| R$_1$, wR$_2$ [all data] | 0.0896, 0.2627 |
| Largest diff. peak and hole (e Å$^{-3}$) | 1.12, −0.44 |

Example 3: Gas Absorption Properties of Metal Organic Frameworks

An organic linker containing pyrimidine group (Scheme 1) which was synthesized and structurally characterized its copper MOF [Cu$_2$L(H$_2$O)$_2$].5DMF.3H$_2$O (described hereafter as UTSA-76). UTSA-76 is isostructural to NOTT-101, so these two MOFs have the comparable porosities and saturated methane storage capacities. However, UTSA-76 had much higher methane storage capacity than NOTT-101 at 65 bar and room temperature. UTSA-76 obtained a volumetric methane storage of 259 cm$^3$ (STP) cm$^{-3}$ at 65 bar and room temperature. UTSA-76 had a working capacity of 199 cm$^3$ (STP) cm$^{-3}$ at room temperature. Compared with HKUST-1 for methane storage, generally, UTSA-76 had a higher working capacity, but also exhibited a higher gravimetric energy density and gravimetric working capacity than HKUST-1.

SCHEME 1: Schematic structure of the organic ligands that serve as linkers in UTSA-76 (a) and NOTT-101 (b).

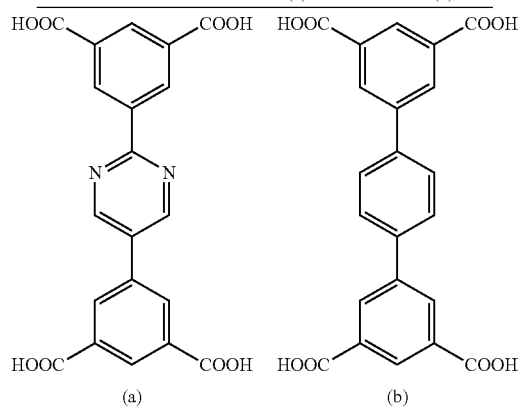

Figure 3:
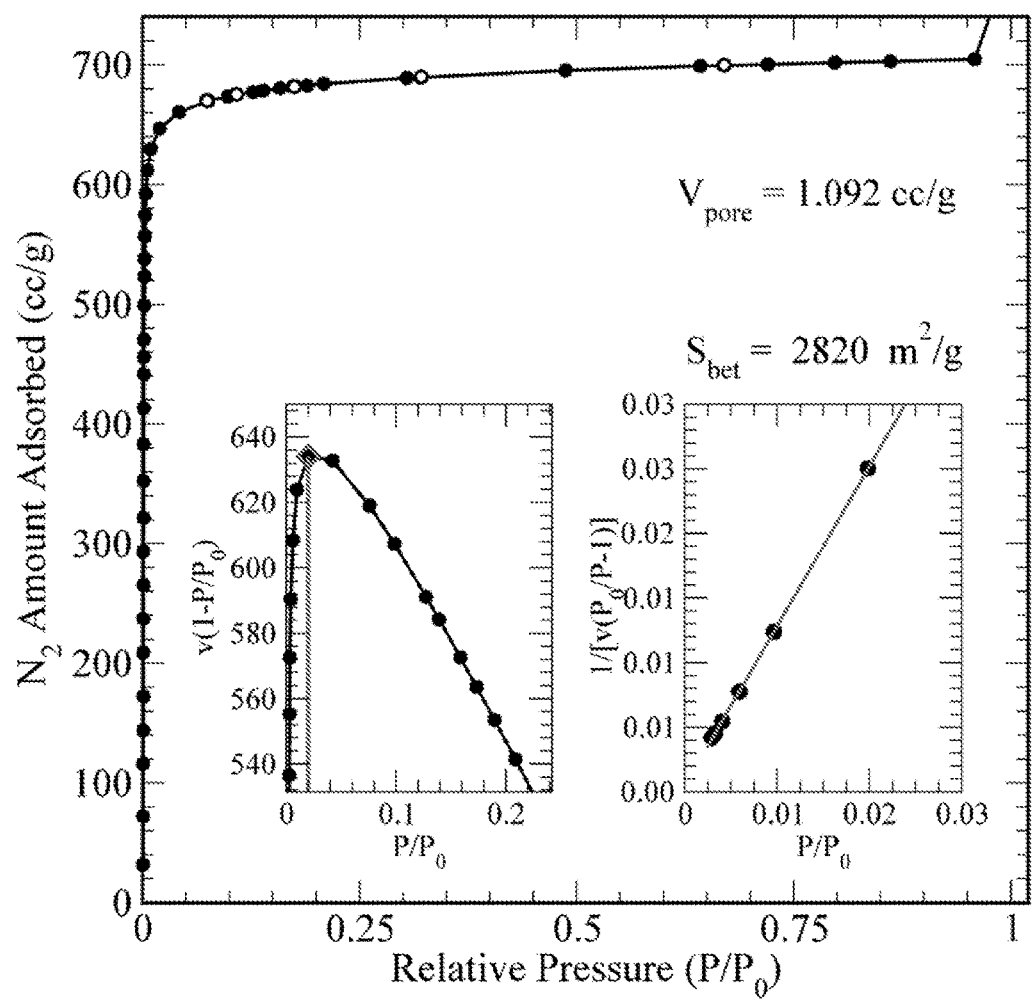
FIG. 3 shows nitrogen isotherm at 77 K with consistency and BET plots for the activated UTSA-76a sample.

Acetone-exchanged UTSA-76 was activated at room temperature for 24 h, and then at 373 K under high vacuum to yield the activated UTSA-76. The porosity was characterized by nitrogen sorption at 77 K. The N$_2$ isotherm showed reversible Type-I sorption behavior, characteristic for the microporous materials with N$_2$ uptake of 698.2 cm$^3$ g$^{-1}$ (FIG. 3). The Brunauer-Emmett-Teller (BET) surface area of UTSA-76 was 2820 m$^2$ g$^{-1}$, and the pore volume calculated from the maximum amount of N$_2$ adsorbed was 1.092 cm$^3$ g$^{-1}$, which are comparable to those of NOTT-101 (Table 1).

Figure 4:
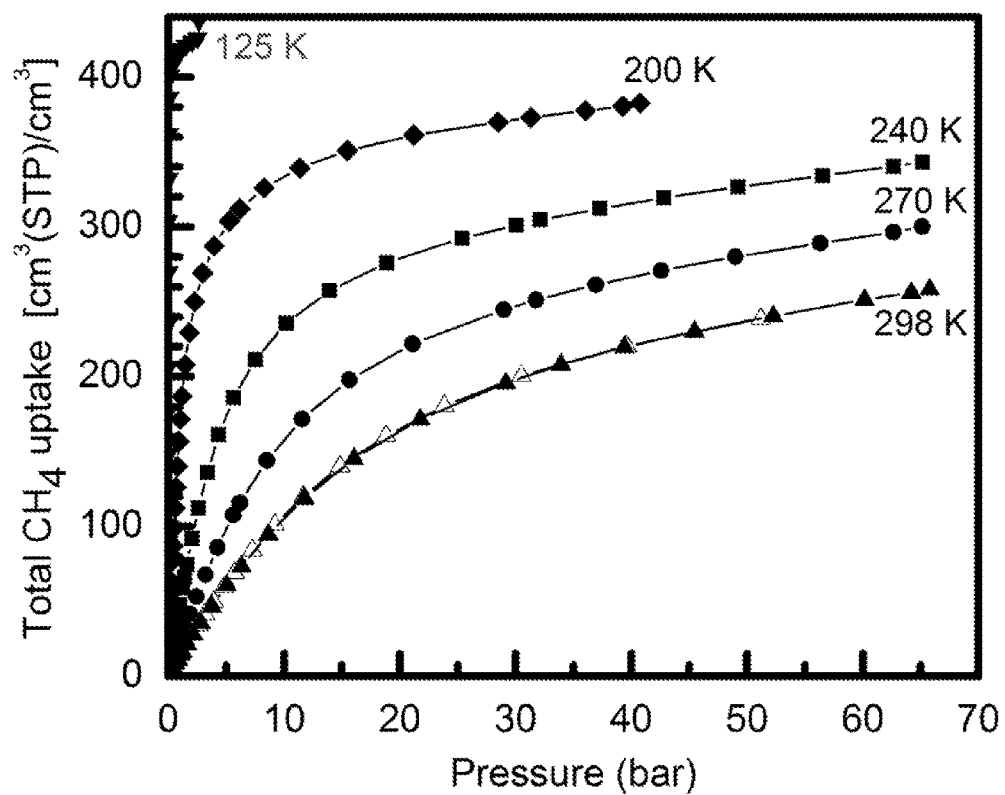
FIG. 4 shows the total volumetric high-pressure methane sorption isotherms of UTSA-76 at different temperatures. Filled and open symbols represent adsorption and desorption data, respectively.

The high surface area, large pore volume, open copper sites and pyrimidine groups within the framework of UTSA-76 prompted examination of its capacity for high-pressure CH$_4$ storage. Temperature-dependent total methane sorption isotherms for UTSA-76 are shown in FIG. 4. At 125 K and 2.2 bar, the absolute methane adsorption of UTSA-76 reached 421.3 cm$^3$ (STP) cm$^{-3}$ corresponding to an adsorbed methane density of 0.301 g cm$^{-3}$, which is 71.2% of that of liquid methane (0.423 g cm$^{-3}$) at 113 K. UTSA-76 exhibited an absolute methane uptake of 259 cm$^3$ cm$^{-3}$ at 298 K and 65 bar, which almost meets the DOE target of 263 cm$^3$ (STP) cm$^{-3}$. Furthermore, the total gravimetric methane uptake of UTSA-76 was 0.264 g/g, which corresponds to 52.8% of the DOE's gravimetric target of 0.5 g/g.

Figure 5:
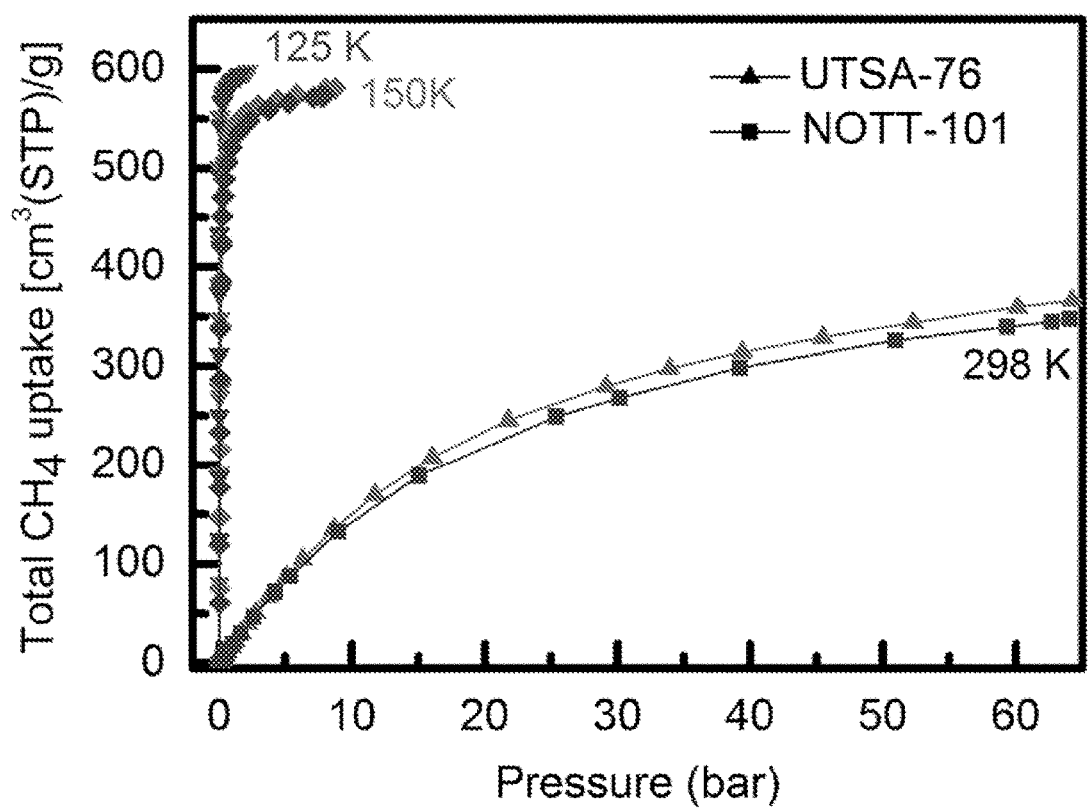

HKUST-1 represents the standard for volumetric methane storage at room temperature and 65 bar with a volumetric methane storage of 267 cm$^3$ (STP) cm$^{-3}$ and the methane storage of UTSA-76 was compared to HKUST-1. As shown in FIG. 4, the volumetric methane uptake of UTSA-76 was only slightly lower than HKUST-1, while the gravimetric uptake (0.264 g/g) was higher than HKUST-1 (0.216 g/g). Without wishing to be bound by any theory, the enhancement on the gravimetric methane uptake of UTSA-76 can be attributed to its larger surface area and pore volume compared with those of HKUST-1. Additionally, the methane uptake values of UTSA-76 and NOTT-101 were compared due to their similar structure (Table 2 and FIG. 5). It was found that both total volumetric and gravimetric methane uptakes of UTSA-76 are higher than those of NOTT-101

Figure 6:
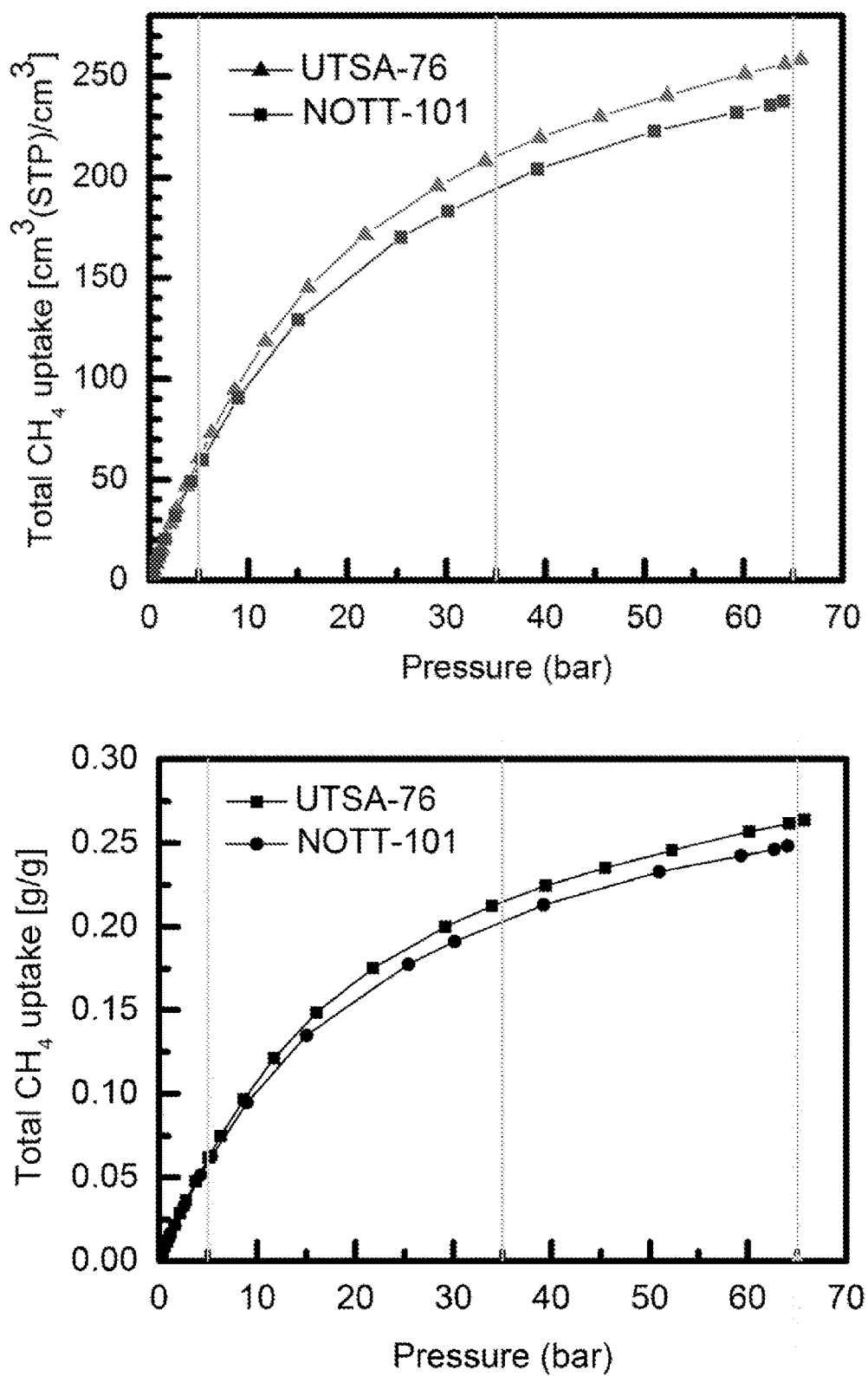

(FIG. 6). Without wishing to be bound by any theory, the pyrimidine groups in UTSA-76 are believed to be beneficial for its methane uptake.

TABLE 2

Comparison of some microporous MOFs for the high-pressure methane storage at room temperature and 65 bar.

| MOFs | $S_{BET}{}^a$ m² g⁻¹ | $V_p{}^b$ cm³ g⁻¹ | $D_c{}^c$ g cm⁻³ | Total uptake$^d$ at 65 bar g g⁻¹ | Total uptake$^d$ at 65 bar cm³ cm⁻³ | density | Working capacity$^e$ at 65 bar g g⁻¹ | Working capacity$^e$ at 65 bar cm³ cm⁻³ | Initial $Q_{st}$ kJ/mol |
|---|---|---|---|---|---|---|---|---|---|
| UTSA-76 | 2820 | 1.09 | 0.699 | 0.263 | 257 | 0.184 | 0.201 | 197 | 15.44 |
| HKUST-1 | 1850 | 0.78 | 0.883 | 0.216 | 267 | 0.191 | 0.154 | 190 | 17 |
| NOTT-101 | 2805 | 1.08 | 0.688 | 0.247 | 237 | 0.169 | 0.189 | 181 | 15.49 |

$^a$BET surface areas calculated from N₂ isotherms at 77K.
$^b$Pore volumes calculated from the maximum amounts of N₂ adsorbed.
$^c$Framework densities without guest molecules and terminal waters.
$^d$At 298K and 65 bar.
$^e$Defined as the difference of the amount of methane adsorbed between 65 bar and 5 bar.

Figure 7:
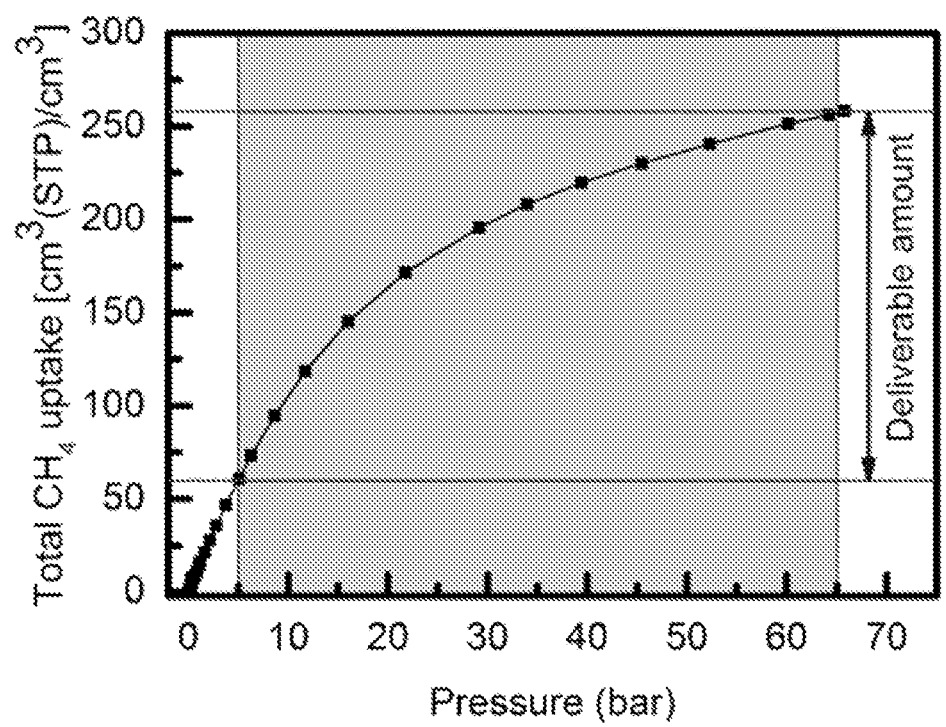
FIG. 7 shows the schematic of the determination of deliverable amount of UTSA-76, defined as the difference in uptake between 65 bar and 5 bar.

Additionally, the working capacity or deliverable capacity determines the driving range of natural gas vehicles (NGVs) and should be evaluated to determine a material's performance. The working capacity is defined here as the difference of the amount of methane adsorbed between 65 bar and 5 bar. For example, a good methane storage material should have a high methane uptake at 65 bar but a low uptake at 5 bar. From Table 1, UTSA-76 exhibited an working capacity of 199 cm³ (STP) cm⁻³, which is ~5% higher than HKUST-1 (190 cm³ (STP) cm⁻³). This working capacity of UTSA-76 was found to be primarily due to its much lower methane uptake at 5 bar (FIG. 7). The relatively low methane uptake in UTSA-76 at low pressure was attributed to its lower initial $Q_{st}$ of $CH_4$ adsorption compared to that of HKUST-1 (Table 1). Furthermore, the gravimetric working capacity of UTSA-76 (0.202 g/g) was higher than that of HKUST-1 (0.154 g/g) mainly due to its comparatively higher gravimetric uptake at 65 bar. In contrast to UTSA-76, the isostructural NOTT-101 showed a lower volumetric working capacity than HKUST-1 (181 cm³ (STP) cm⁻³ vs. 190 cm³ (STP) cm⁻³).

The different methane storage performances including the working capacity, the total volumetric and gravimetric uptakes between UTSA-76 and NOTT-101 motivated exploration into why the introduction of pyrimidine groups can result in an increase in methane storage.

Figure 8:
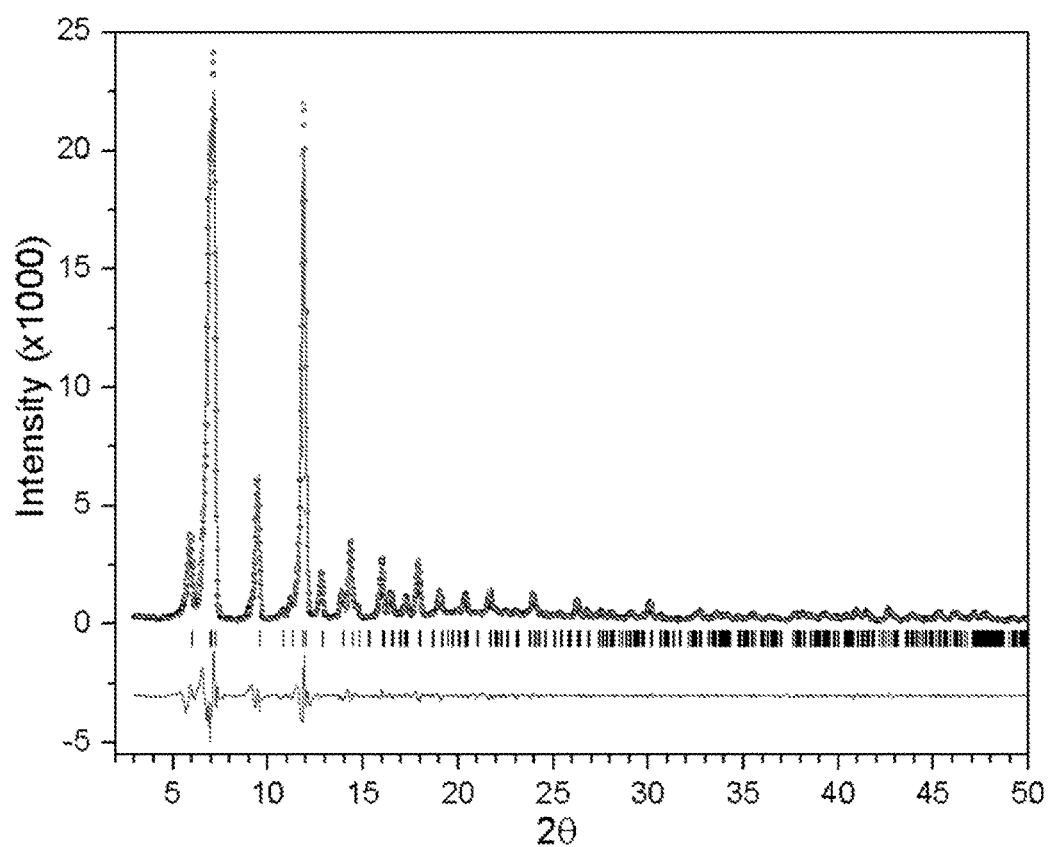
FIG. 8 shows experimental (circles), Le Bail fitted (line), and difference (line below observed and calculated patterns) PXRD profile for activated UTSA-76 at 298 K (Cu Kα radiation). Vertical bars indicate the calculated positions of Bragg peaks. Refined lattice parameters: a=18.574(2) Å and c=38.022(8) Å. Rp=0.071, Rwp=0.090. Corresponding crystal density: 0.699 g/cc.
Figure 9:
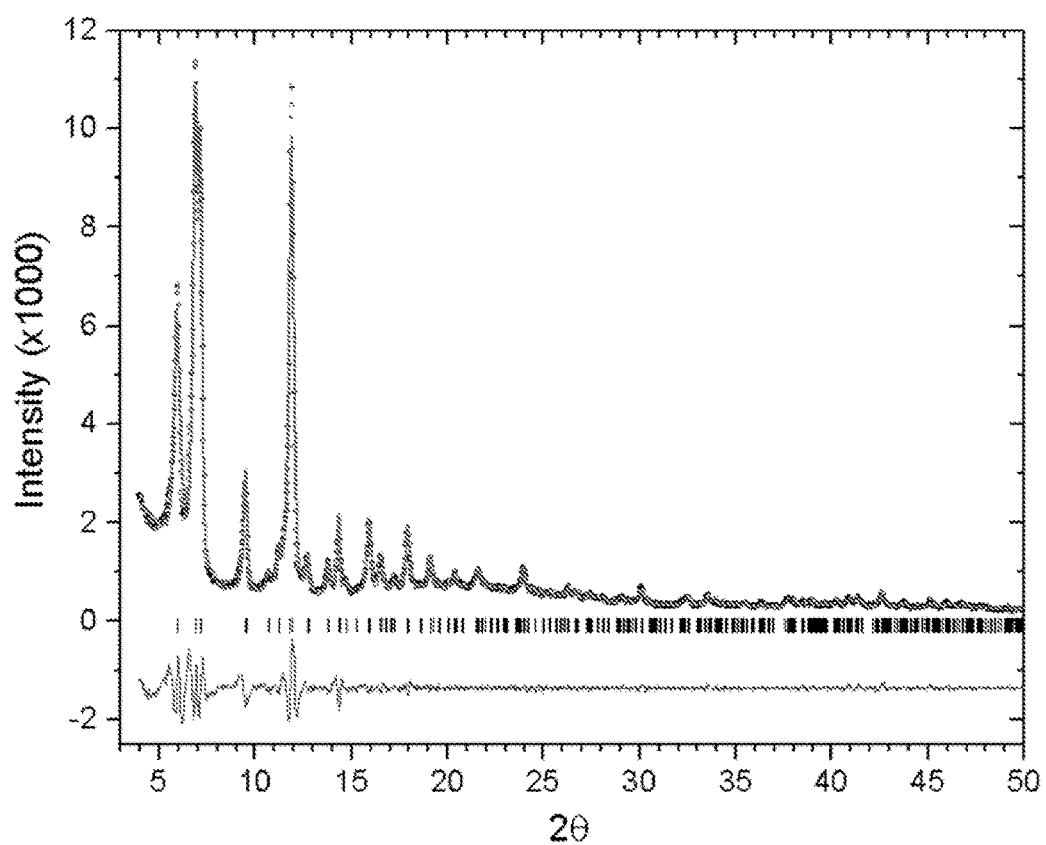
FIG. 9 shows experimental (circles), Le Bail fitted (line), and difference (line below observed and calculated patterns) PXRD profile for activated NOTT-101 at 298 K (Cu Kα radiation). Vertical bars indicate the calculated positions of Bragg peaks. Refined lattice parameters: a=18.578(2) Å and c=38.469(8) Å. Rp=0.071, Rwp=0.090. Corresponding crystal density: 0.688 g/cc.
Figure 10:
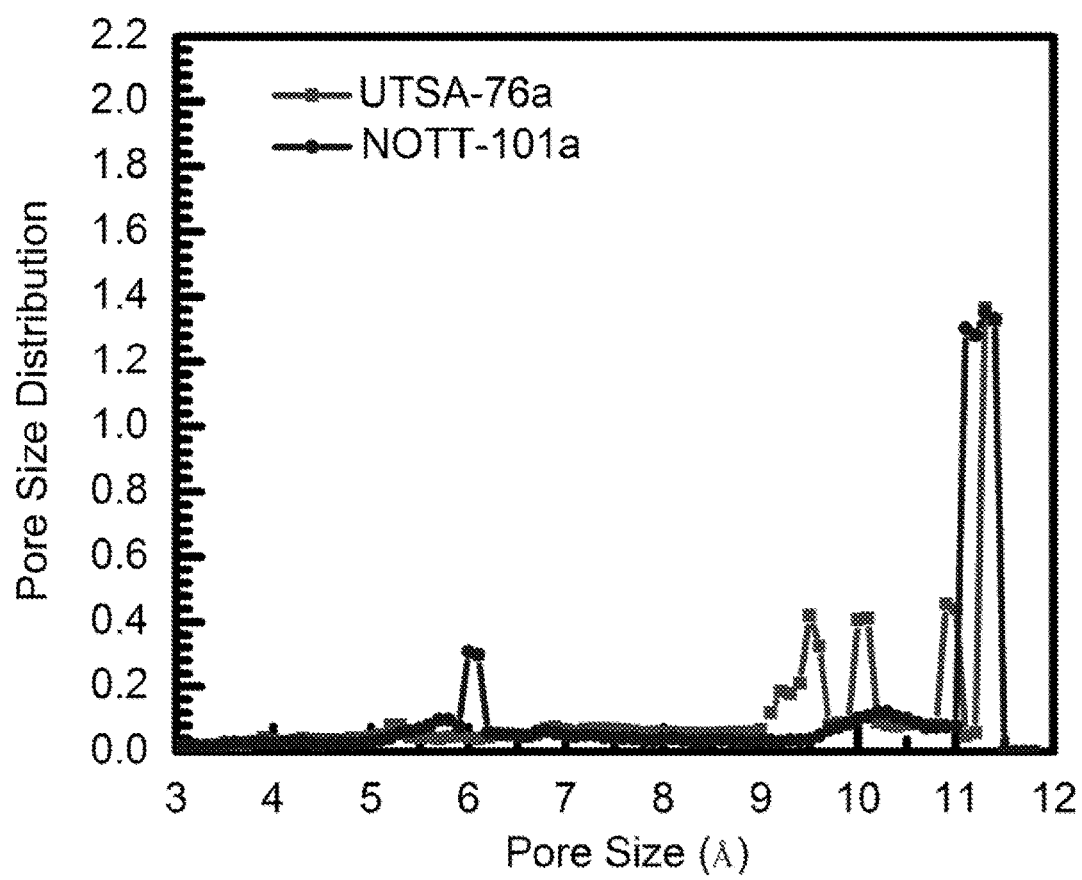
FIG. 10 shows pore size distributions (PSDs) of UTSA-76a and NOTT-101a. PSDs were calculated using the method of Gubbins et al (Spek, 1999). The van der Waals diameters of the framework atoms were adopted from the Cambridge Crystallographic Centre.

To investigate the improved methane storage performance of UTSA-76 was compared to NOTT-101, the two MOFs were examined from structural perspective. Experimental x-ray diffraction data showed that the two MOFs are isostructural with same crystal symmetry (R-3m). Lattice parameters of the fully activated samples were close, with a being almost identical and c differing by ~1.2% (FIGS. 8 and 9). Consequently, the theoretical crystal densities, pore volumes, surface areas of the two were similar. Introducing pyrimidine groups to the linker did not alter the overall MOF pore structure, and the difference in methane adsorption of the two MOFs was not due to a change in pore geometry. Both of our UTSA-76 and NOTT-101 samples are highly crystalline, and the experimental pore volumes obtained from 77K $N_2$ adsorption data are comparable to their corresponding theoretical pore volumes, the methane adsorption capacity difference was not from sample quality variation (FIG. 10). The possibility of amount of structural vacancies present in the MOF samples was also be ruled out, since no monocarboxylate modulator or co-assembler (which was known to promote linker vacancies) was used in either NOTT-101 or UTSA-76 synthesis (Park et al., 2012 and Wu et al., 2013). The reported volumetric uptake values were converted from the experimental gravimetric uptake values using the ideal crystal densities. The volumetric uptake values (different by ~9%) can be affected by the deviation of the true crystal densities, however, gravimetric uptakes are reliable since the gravimetric uptakes are obtained via measurement. The ~7% difference between the two MOFs' gravimetric methane uptake suggested, without wishing to be bound by any theory, that the improved methane storage performance of UTSA-76 has a structural origin.

The adsorption energy of $CH_4$ was explored as a possible reason for the methane adsorption isotherm difference. First-principles DFT-D (dispersion-corrected density-functional theory) calculations were carried out, where van der Waals (vdW) interactions were corrected by empirical r-6 terms (Giannozzi et al., 2009). Structural optimizations were first performed on UTSA-76 and NOTT-101 structures. The relaxed static structures of the two were similar. $CH_4$ molecules were introduced into the MOF structures. For other Cu-MOFs with similar crystal structures, the previous combined neutron diffraction, GCMC and DFT studies have shown that the open Cu sites and cage window sites are the two primary $CH_4$ adsorptions sites (Wu et al., 2010). For UTSA-76 and NOTT-101, these major $CH_4$ adsorptions sites are the same. Adsorption of methane on the linker surfaces are generally weaker secondary adsorption. The calculations showed that $CH_4$ molecules adsorbed next to the pyrimidine sites of UTSA-76 exhibited similar binding energies as those adsorbed on the central phenyl ring of NOTT-101. No new adsorption sites were found in UTSA-76 introduced by the pyrimidine sites. For static structures of the two MOFs, without wishing to be bound by any theory, the calculated adsorption affinity on the linker pore surface were similar and likely not the reason for the different methane storage performance.

Figure 11:
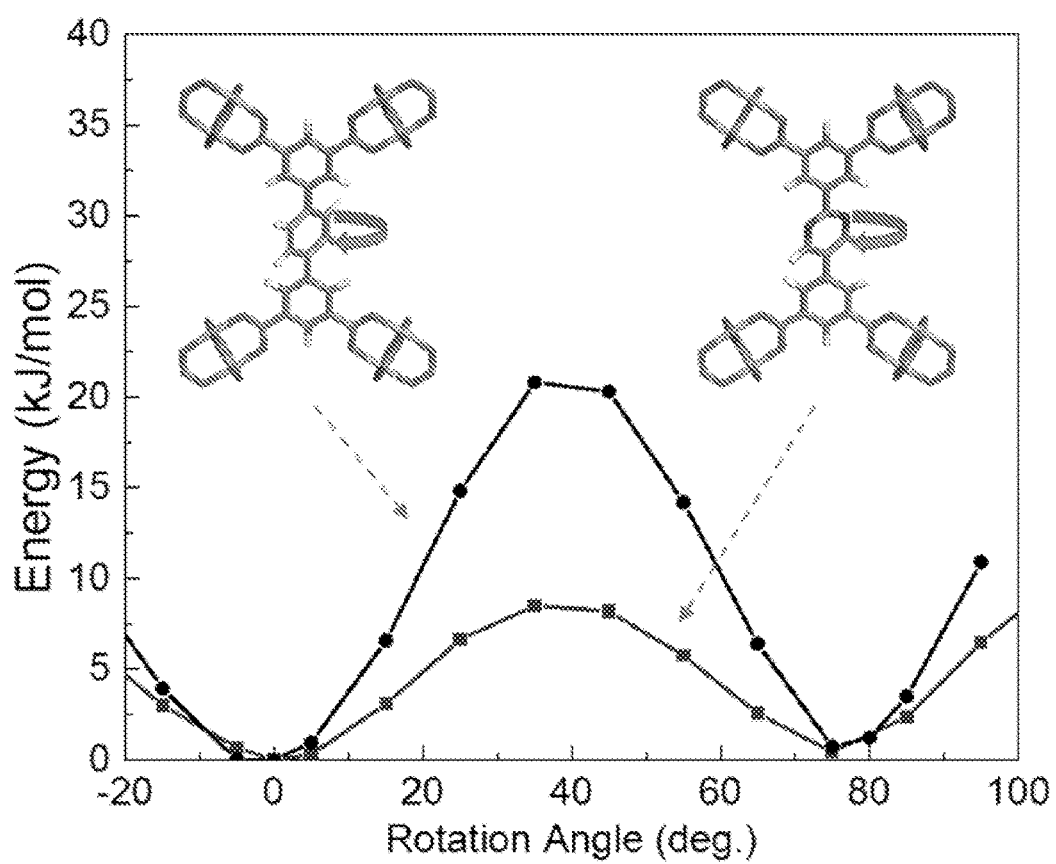
FIG. 11 shows the variation of the total energy as the central rings of the UTSA-76 and NOTT-101 linker are rotated around the linker backbone, derived from DFT calculations. The rotational barrier for UTSA-76 is particularly small, less than half of that for NOTT-101

Similar to other non-flexible Cu-MOFs, NOTT-101 and UTSA-76 have relatively rigid framework structures and, without wishing to be bound by theory, the crystal structures often remain generally unchanged upon gas adsorption/desorption in contrast to highly flexible MOFs. Without wishing to be bound by any theory, the central rings of the linkers had relatively large rotational freedom, which may affect methane storage to certain extent. The energy cost of a rotational motion around two equivalent orientations of the central rings was calculated. The UTSA-76 linker central ring was found to have a shallower rotational barrier (~8.2 kJ/mol vs. ~20.2 kJ/mol, FIG. 11), and thus was significantly more "flexible" than the NOTT-101 linker central ring. As a reference, the calculated rotational barrier for the π-flipping of the benzene group in the well-studied MOF-5 was significantly higher, ~55 kJ/mol (Zhou and Yildirim, 2006). Upon methane adsorption at room temperature, without wishing to be bound by any theory, the central rings of UTSA-76 may adjust their orientations in a harmonic way, to maximize the methane-framework interactions and accommodate more methane molecules.

Figure 12:
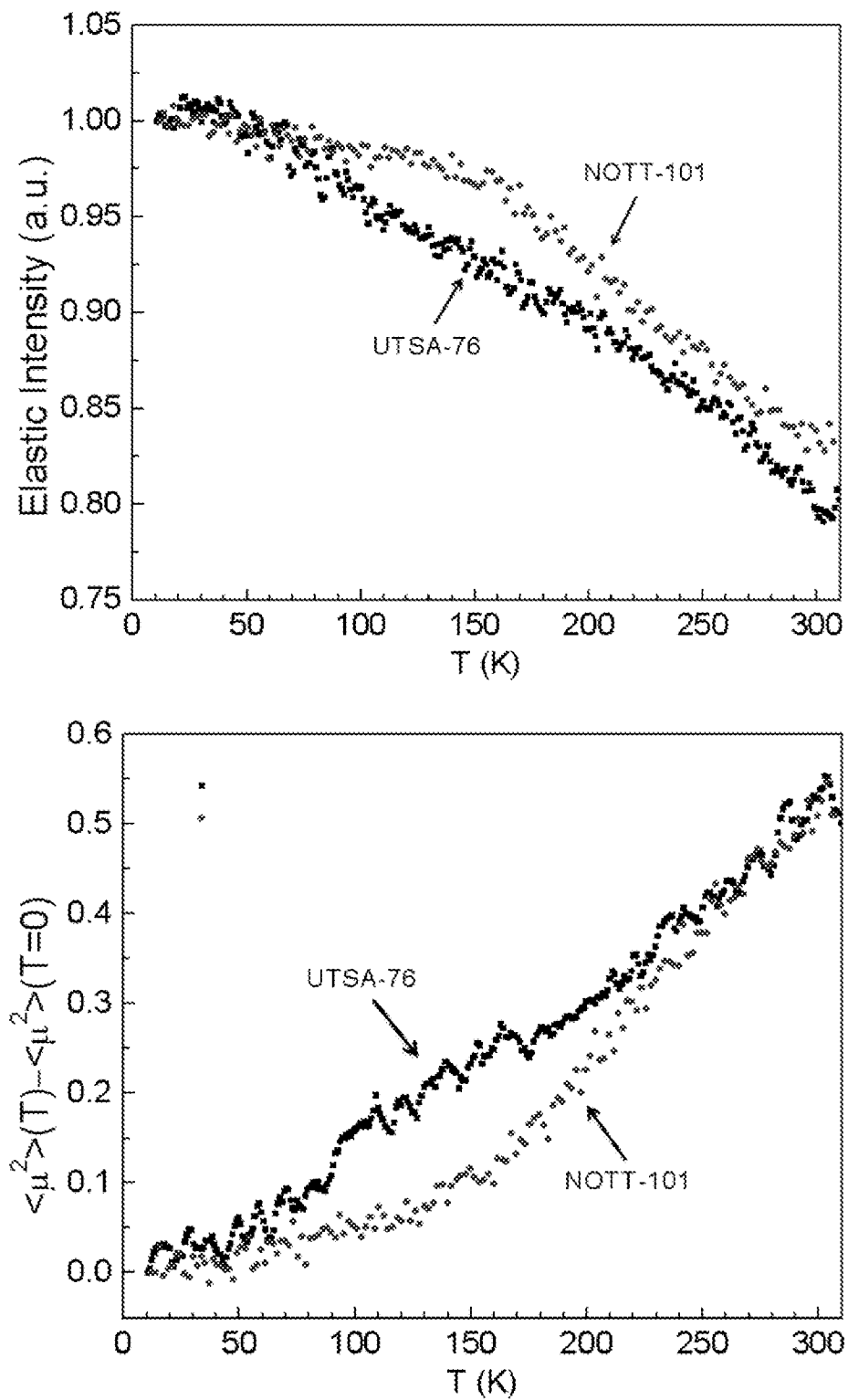
FIG. 12 shows on the top: A comparison of the normalized elastic neutron scattering intensity vs. temperature for UTSA-76a and NOTT-101a and on the bottom: Temperature-dependent atomic mean-square-displacements, derived from data in the top panel.

To experimentally confirm the central linker ring in UTSA-76 had higher rotational freedom, neutron scattering measurements were performed. Neutron scattering is dominated by incoherent scattering from hydrogen atoms. For both UTSA-76 and NOTT-101, the H atoms on the phenyl rings of both end of the linker typically do not have additional movement except thermal motion, because of the restriction of the two carboxylate linkage to the metal centers. In contrast, the H atoms on the central rings have additional motions such as but not limited to librations, two-site jumping, or π-flipping of the central ring. Neutron scattering was used to probe the H motion on the central rings of the MOF linker. Elastic scans of the neutron scattering intensity vs. temperature for UTSA-76 and NOTT-101 were conducted, from which, the temperature-dependent atomic mean-square displacements were derived (FIG. 12). The rotational motion of the UTSA-76 central ring was found to enter the time scale window accessible by the spectrometer (~$10^{-8}$ s) at much lower temperature than the NOTT-101 central ring (~70 K vs. ~150 K). These data showed that the UTSA-76 central ring indeed has higher mobility than NOTT-101, which agreed with the DFT calculations that suggest a much lower rotational barrier for NOTT-101.

Figure 13:
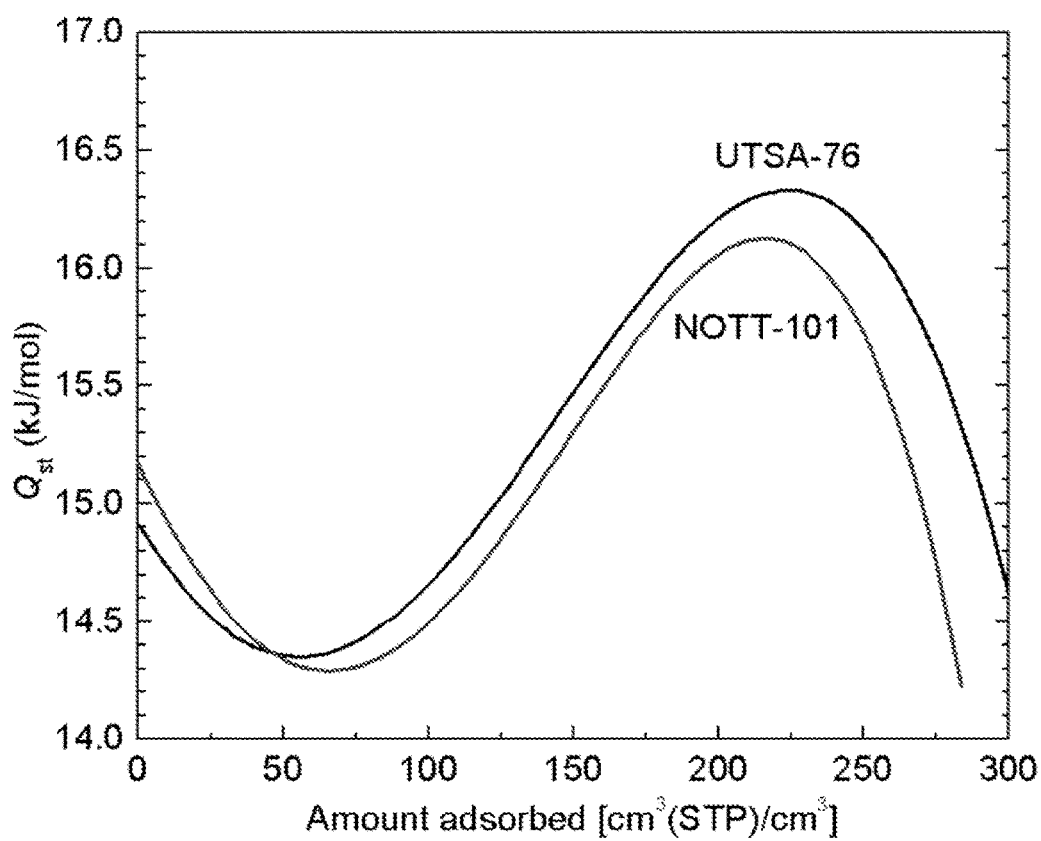
FIG. 13 shows the comparison of $Q_{st}$ for $CH_4$ adsorption for UTSA-76 and NOTT-101.
Figure 14:
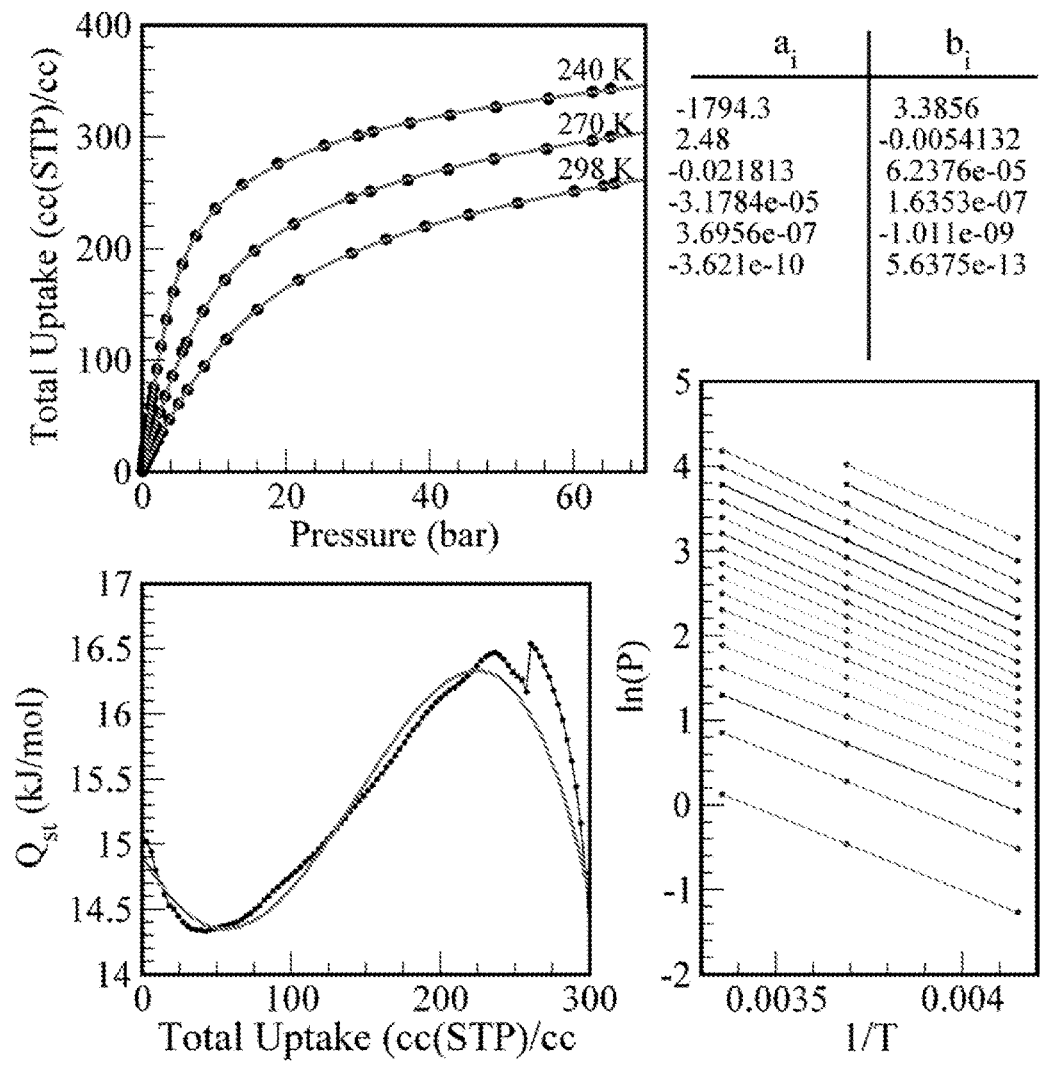
FIG. 14 shows the derivation of $Q_{st}$ for $CH_4$ adsorption for UTSA-76a. The gray line in the $Q_{st}$ plot is obtained from virial fitting of the absolute adsorption isotherm data. The fit and the virial coefficients are also shown. The black line in the $Q_{st}$ plot is obtained from the raw isotherm data using cubic spline method without any fitting.
Figure 15:
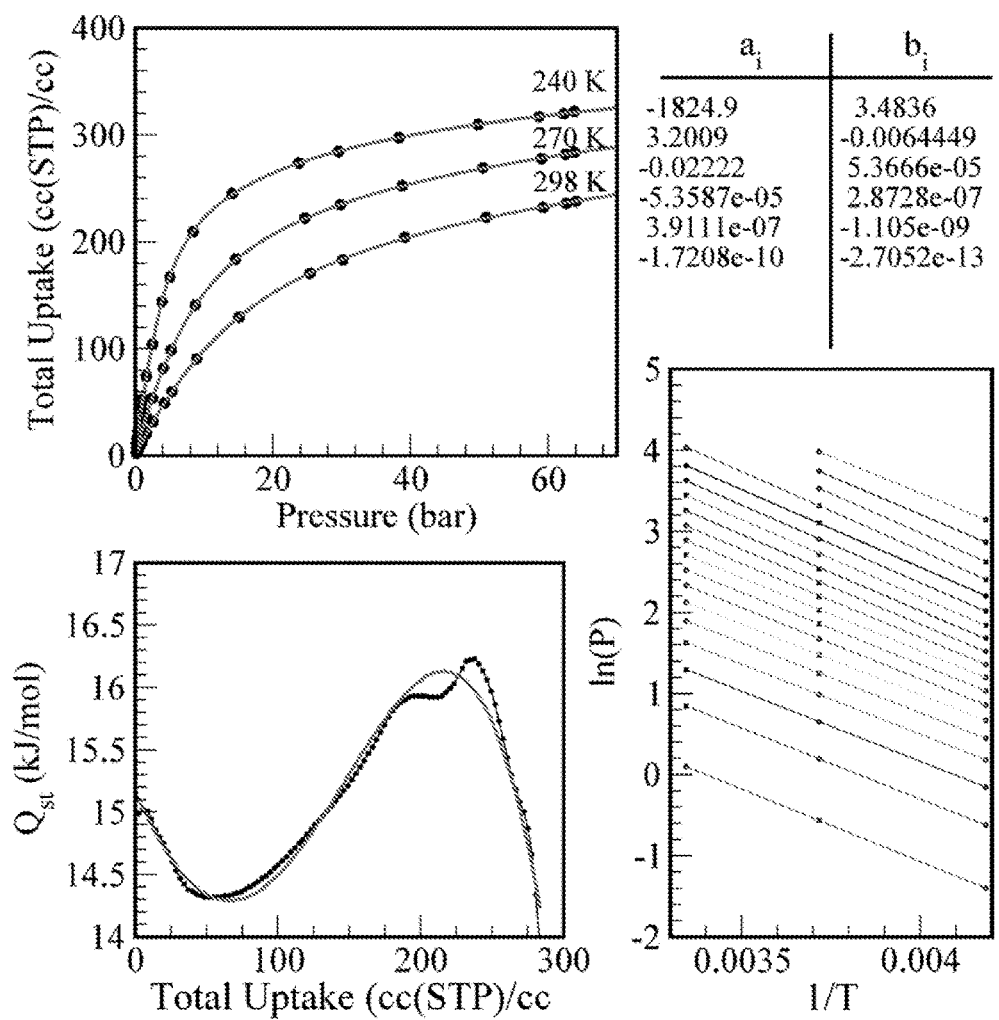
FIG. 15 shows the derivation of $Q_{st}$ for $CH_4$ adsorption for NOTT-101a. The gray line in the $Q_{st}$ plot is obtained from virial fitting of the absolute adsorption isotherm data. The fit and the virial coefficients are also shown. The black line in the $Q_{st}$ plot is obtained from the raw isotherm data using cubic spline method without any fitting.
Figure 16:
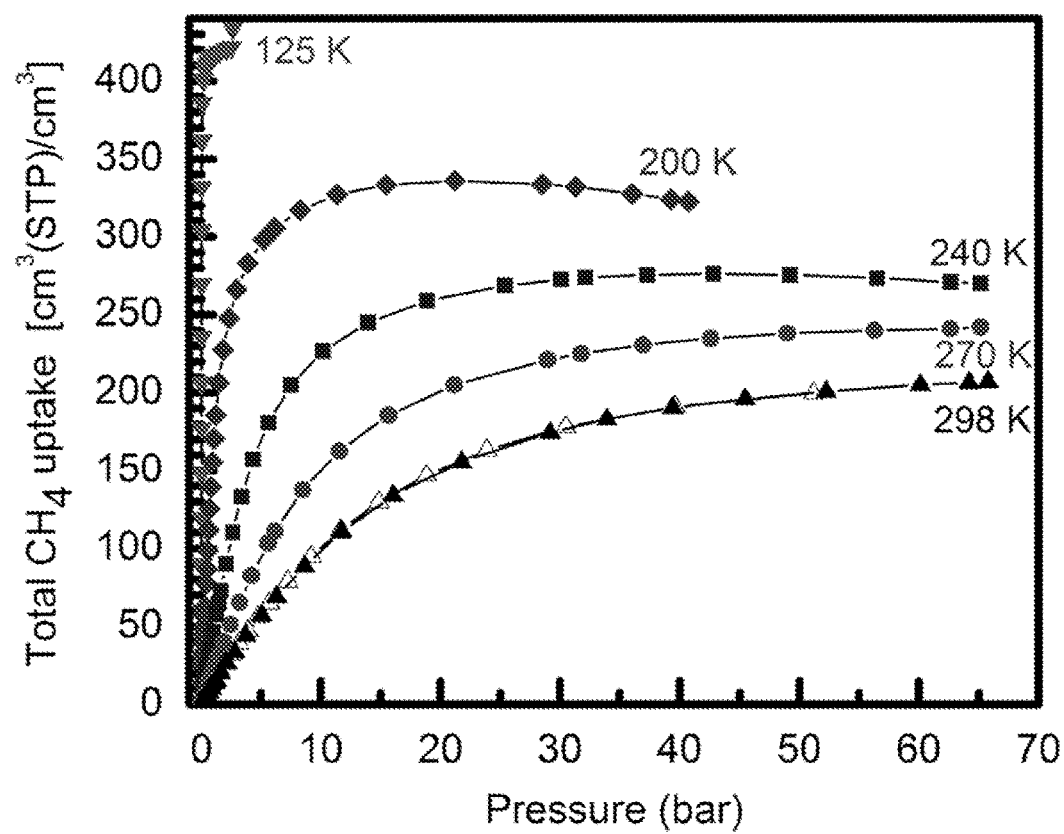
FIG. 16 shows excess volumetric high-pressure methane sorption isotherms of UTSA-76 at different temperatures. Filled and open symbols represent adsorption and desorption data, respectively.

Without being bound by theory, the higher central ring rotational freedom is believed to likely be responsible for the enhanced methane storage performance of UTSA-76. This observation was in line with the fact that the experimental $Q_{st}$ of methane adsorption in the two MOFs are quite close, with $Q_{st}$(UTSA-76) being only slightly higher than $Q_{st}$(NOTT-101) at high methane loading (FIGS. 13-15).

Example 4: Additional Ligands

In some embodiments, the invention provides MOFs based on one or more of the ligands having the formulas listed below, or partially or completely pronated forms thereof:

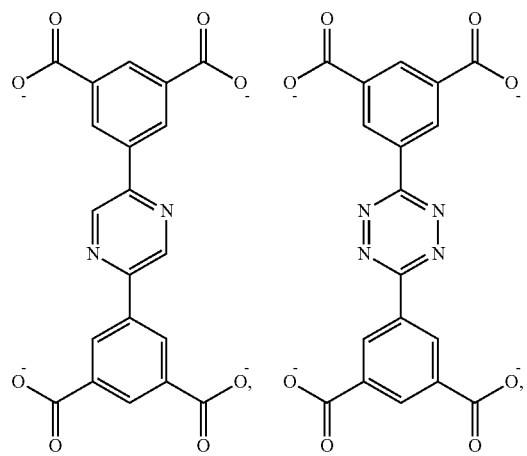

-continued

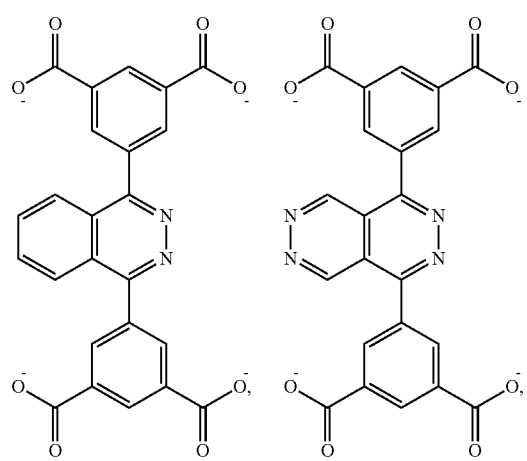

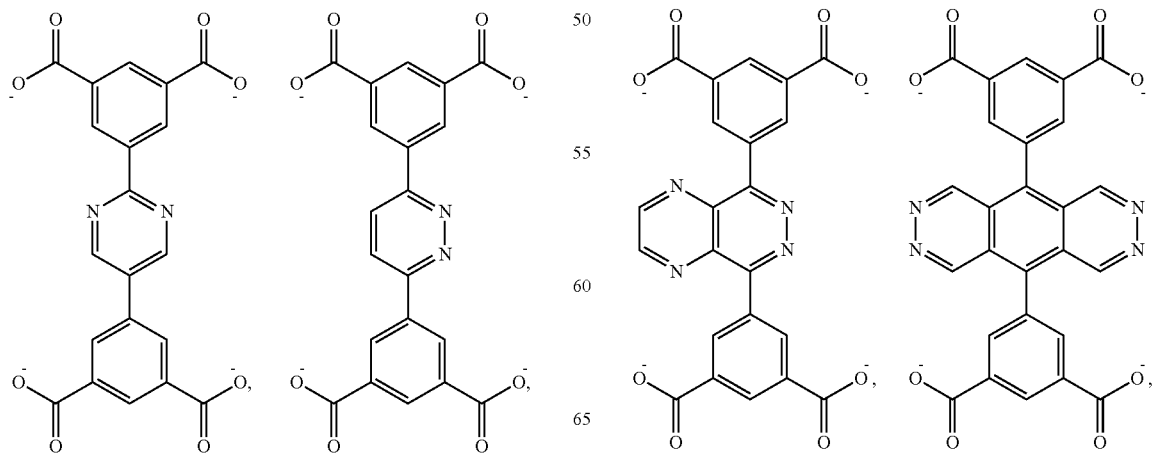

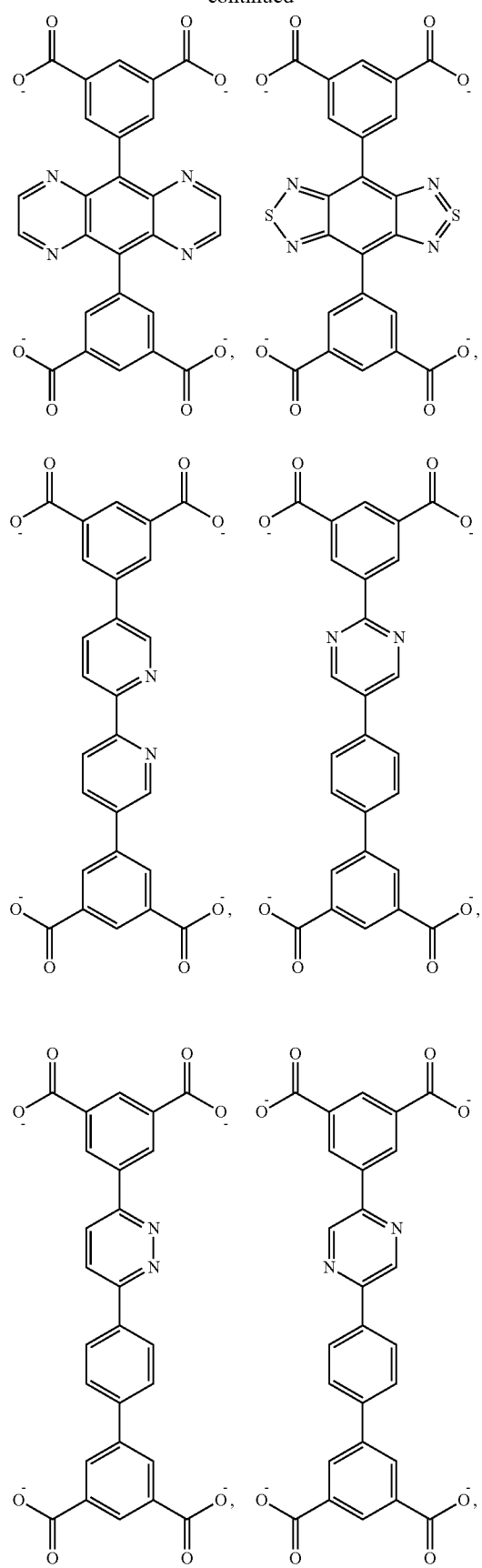
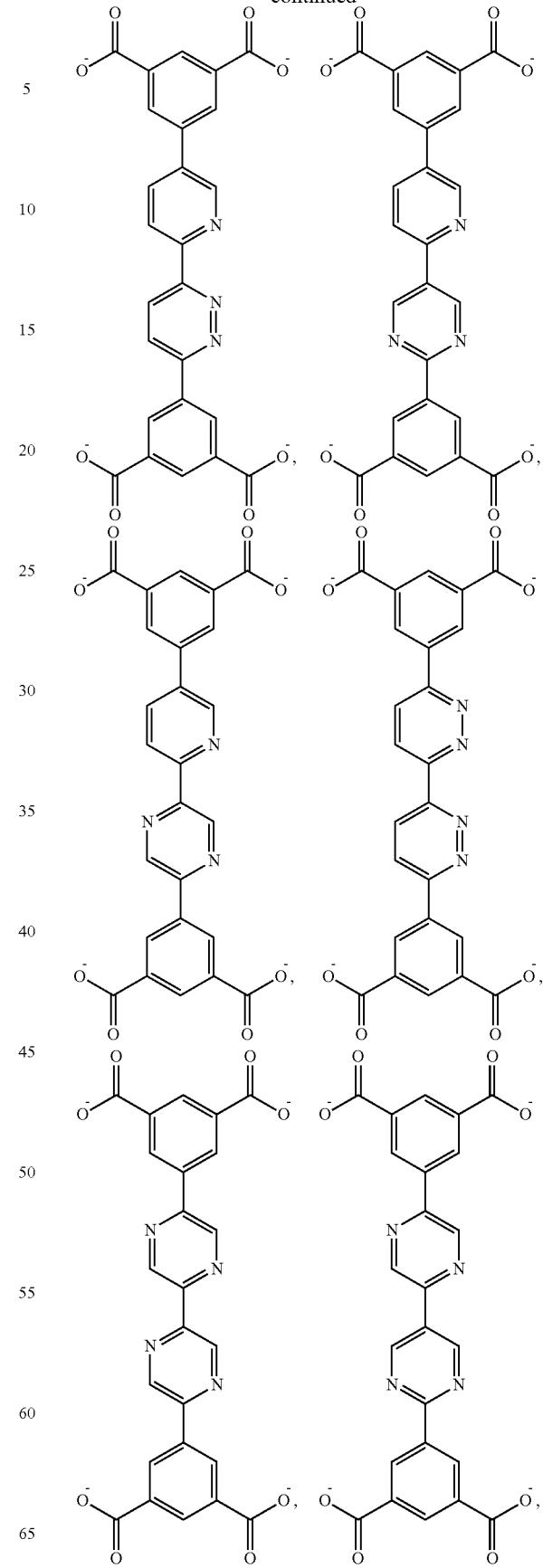

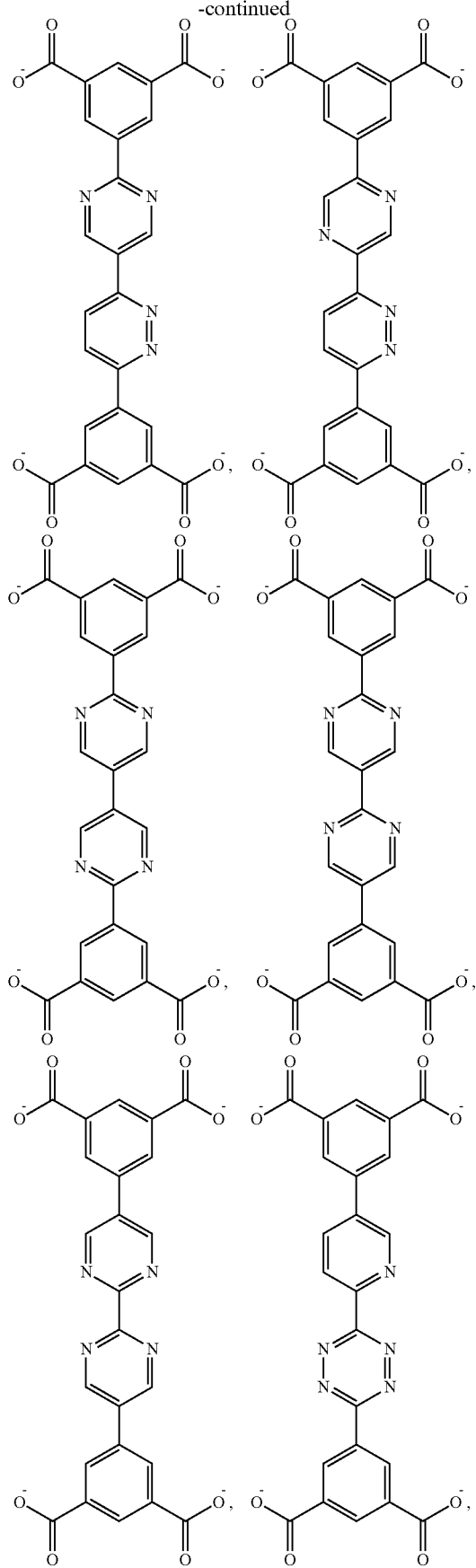
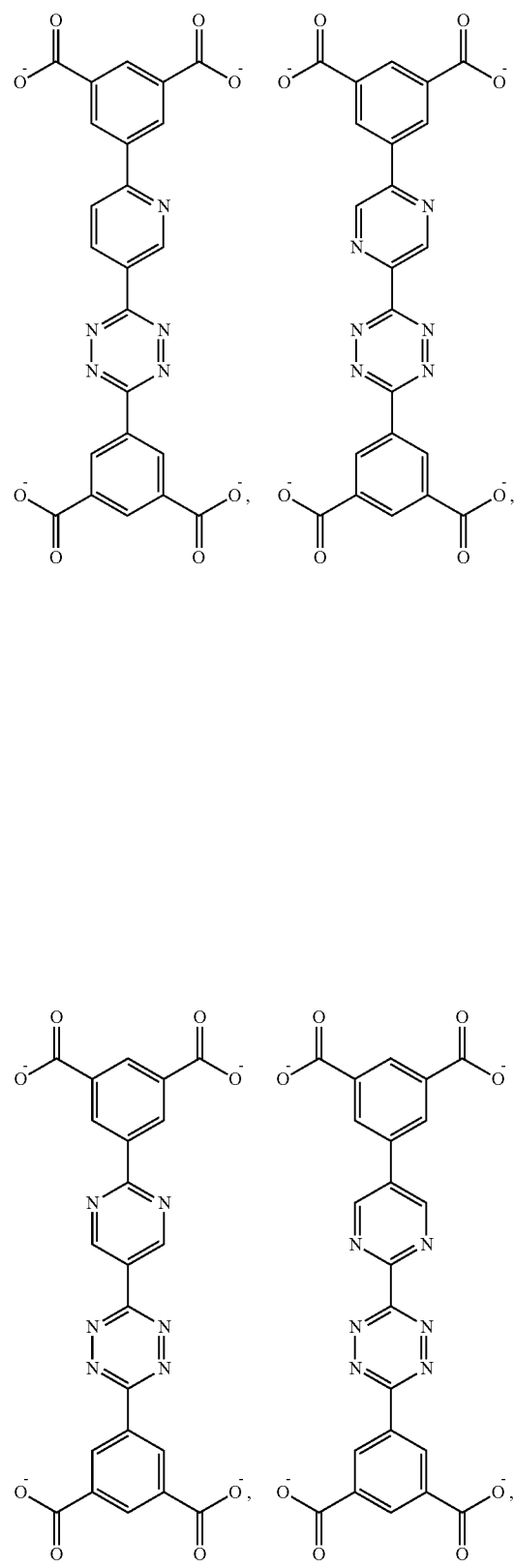

-continued

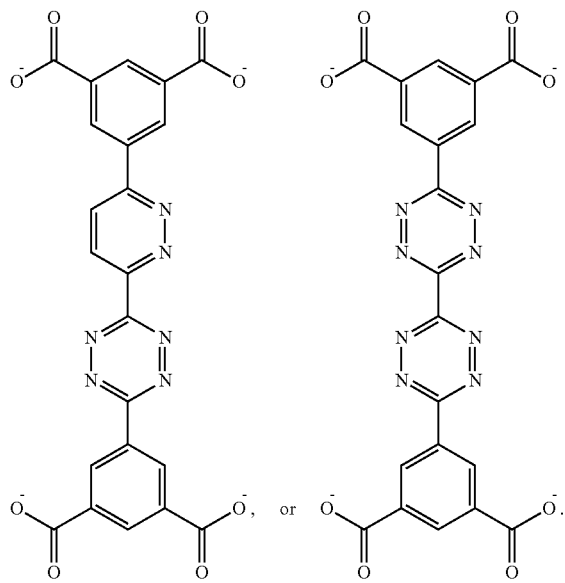 [SMILES: O=C(O)c1cc(C(=O)O)cc(-c2ccc(-c3nnc(-c4cc(C(=O)O)cc(C(=O)O)c4)nn3)nn2)c1 ; O=C(O)c1cc(C(=O)O)cc(-c2nnc(-c3nnc(-c4cc(C(=O)O)cc(C(=O)O)c4)nn3)nn2)c1]

REFERENCES

The following references, to the extent that they provide exemplary procedural or other details supplementary to those set forth herein, are specifically incorporated herein by reference.

Armor, J. N. *J. Energy Chem.* 22, 21, 2013.
BASF Energy Storage Metal Organic Framework (MOF) Materials.
Bhattacharya and Gubbins, *Langmuir*, 22, 7726-7731, 2006.
Chen et al., *Angew. Chem., Int. Ed.*, 44, 4745, 2005.
Chen et al., *Cryst. Growth Des.*, 10, 2775-2779, 20100.
Chui et al., *Science*, 283, 1148, 1999.
DOE MOVE Program Guidelines, 2012.
Eddaoudi et al., *Science*, 295, 469, 2002.
Feldblyum et al., *Langmuir*, 29, 8146, 2013.
Férey et al., *Chem. Soc. Rev.*, 38, 1380, 2009.
Gedrich et al., *Angew. Chem., Int. Ed.*, 49, 8489, 2010.
Getman et al., *Chem. Rev.*, 112, 703, 2012.
Giannozzi et al., *J. Phys.: Condens. Matter*, 21, 395502, 2009.
Guo et al., *Angew. Chem., Int. Ed*, 50, 3178. 2011.
He et al., *Chem. Commun.*, 48, 11813, 2012.
He et al., *Energy Environ. Sci.*, 6, 2735, 2013.
Horike et al., *Nat. Chem.*, 1, 695, 2009.
Jiang and Xu, *Chem. Commun.*, 47, 3351-3370, 2011.
Kondo et al., *Angew. Chem., Int. Ed.*, 36, 1725, 1997.
Kong et al., *Chem. Eur. J.*, 19, 14886, 2013.
Lin et al., *Angew. Chem., Int. Ed.*, 45, 7358, 2006.
Ma et al., *Am. Chem. Soc.*, 130, 1012, 2008.
Makal et al., *Chem. Soc. Rev.*, 41, 7761, 2012.
Mason et al., *Chem. Sci.*, 5, 32, 2014.
Meyer et al., *Rev. Sci. Instrum.*, 74, 2759-2777, 2003.
O'Keeffe et al., *Chem. Rev.*, 112, 675 2012.
Park and Suh, *Chem. Sci.*, 4, 685, 2013.
Park et al., *J Am. Chem. Soc.*, 134, 20110, 2012.
Peng et al., *Am. Chem. Soc.*, 135, 11887, 2013.
Sheldrick, G. M. Program for Structure Refinement. Germany, 1997.
Spek, L. PLATON: The University of Utrecht: Utrecht, The Netherlands, 1999.
Sumida et al., *Chem. Rev.*, 112, 724, 2012.
Wang et al., *J. Am. Chem. Soc.*, 135, 13222, 2013.
Wilmer et al., *Energy Environ. Sci.*, 6, 1158, 2013.
Wu et al., *Chem. Rev.*, 112, 836, 2012.
Wu et al., *J. Am. Chem. Soc.*, 131, 4995, 2009.
Wu et al., *J. Am. Chem. Soc.*, 135, 10525, 2013.
Wu et al., W. *Chem. Eur. J.*, 16, 5205, 2010.
Yan et al., *Acc. Chem. Res.*, 10.1021/ar400049h, 2013.
Zhang et al., *Chem. Rev.*, 112, 1001, 2012.
Zhou and Yildirim, *Phys. Rev. B*, 74, 180301(R), 2006.
Zhou et al., *J. Phys. Chem. C*, 111, 16131-16137, 2007.

What is claimed is:

1. A metal-organic framework (MOF) comprising a repeat unit of the formula $[Cu_2L(H_2O)_2]$, wherein L is a ligand of the formula:

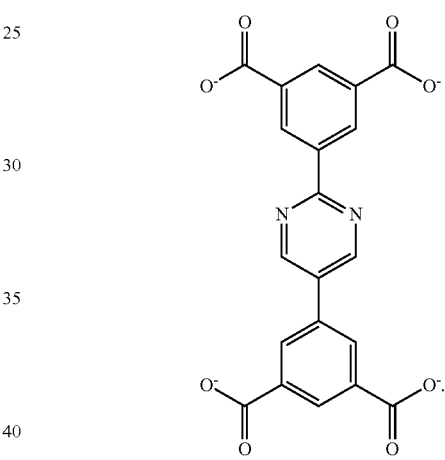

2. The MOF of claim 1, wherein the MOF is activated for sorption of gas molecules.

3. The MOF of claim 1, further comprising one or more than one type of guest molecule.

4. The MOF of claim 1, wherein the repeating formula is further defined as $[Cu_2L(H_2O)_2]\cdot 5DMF\cdot 3H_2O$.

5. The MOF of claim 1, wherein the solvent molecules occupy the pores of the MOF.

6. The MOF of claim 3, wherein one type of guest molecule is a gas molecule.

7. The MOF of claim 6, wherein the gas molecule is $H_2$, $CO_2$, or $CH_4$.

8. The MOF of claim 1, having a weight percentage at least 90% attributable to repeat units of the formula $[Cu_2L(H_2O)_2]\cdot 5DMF\cdot 3H_2O$.

9. The MOF of claim 1, wherein the MOF has been adhered to a fixed surface.

10. A method of separating two or more compounds using an MOF comprising:
   (a) obtaining a MOF comprising a repeat unit of the formula $[Cu_2L(H_2O)_2]\cdot 5DMF\cdot 3H_2O$, wherein L is a ligand of formula:

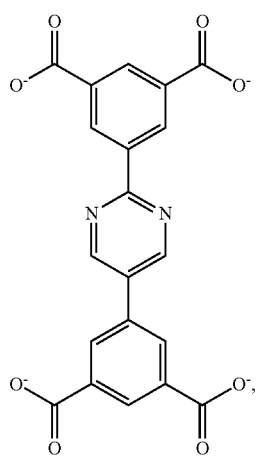

and
- (b) combining the MOF with a mixture comprising a first compound and a second compound; and
- (c) separating the first compound from the second compound.

11. The method of claim 10, wherein the MOF is activated for sorption of gas molecules.

12. The method of claim 10, wherein the first compound is $H_2$.

13. The method of claim 10, wherein the second compound is $CH_4$ or $CO_2$.

14. The method of claim 10, wherein the mixture further comprises a third compound.

15. The method of claim 10, wherein the mixture comprises $H_2$ and $CH_4$.

16. The method of claim 10, wherein the mixture comprises $H_2$ and $CO_2$.

17. The method of claim 10, wherein the separation is carried out at a pressure from about 4 mPa to about 15 mPa.

18. The method of claim 10, wherein the MOF is adhered to a fixed bed surface.

19. The method of claim 10, wherein the MOF is packed in an absorber.

20. A method of using a metal organic framework (MOF), wherein the MOF is an MOF of claim 1 and the MOF is used in an application selected from sensing, heterogeneous catalysis, drug delivery, lithium sulfide battery, membranes, and analytical devices.

* * * * *